United States Patent
Farris et al.

(10) Patent No.: US 11,389,597 B2
(45) Date of Patent: Jul. 19, 2022

(54) STAGED TELESCOPIC SCREW ASSEMBLY HAVING DIFFERENT VISUAL INDICATORS

(71) Applicant: West Pharma. Services IL, Ltd., Ra'anana (IL)

(72) Inventors: Jason W. Farris, Gilbert, AZ (US); Jorge Santos, Scottsdale, AZ (US); Marla Meyer, Tempe, AZ (US); Anthony G. Esposito, Fountain Hills, AZ (US)

(73) Assignee: West Pharma. Services IL, Ltd., Ra'anana (IL)

( * ) Notice: Subject to any disclaimer, the term of this patent is extended or adjusted under 35 U.S.C. 154(b) by 0 days.

(21) Appl. No.: 16/085,274

(22) PCT Filed: Mar. 16, 2017

(86) PCT No.: PCT/US2017/022639
§ 371 (c)(1),
(2) Date: Sep. 14, 2018

(87) PCT Pub. No.: WO2017/161076
PCT Pub. Date: Sep. 21, 2017

(65) Prior Publication Data
US 2019/0060578 A1    Feb. 28, 2019

Related U.S. Application Data

(60) Provisional application No. 62/309,111, filed on Mar. 16, 2016.

(51) Int. Cl.
*A61M 5/315* (2006.01)
*F16H 25/20* (2006.01)

(52) U.S. Cl.
CPC .... *A61M 5/31586* (2013.01); *A61M 5/31511* (2013.01); *A61M 5/31581* (2013.01);
(Continued)

(58) Field of Classification Search
CPC .......... A61M 5/31586; A61M 5/31511; A61M 5/31581; A61M 5/31583; A61M 5/31528;
(Continued)

(56) References Cited

U.S. PATENT DOCUMENTS

| 232,432 A | 9/1880 | Allison |
| 1,125,887 A | 1/1915 | Schimmel |

(Continued)

FOREIGN PATENT DOCUMENTS

| CN | 1505535 A | 6/2004 |
| CN | 1747683 A | 3/2006 |

(Continued)

OTHER PUBLICATIONS

Copaxone®, Innovative Drugs, Teva Pharmaceuticals, downloaded from webpage: http://tevapharm.com/copaxone/, Download date: Jan. 2009, original posting date: unknown, 3 pages.

(Continued)

*Primary Examiner* — Tiffany Legette
*Assistant Examiner* — Antarius S Daniel
(74) *Attorney, Agent, or Firm* — BakerHostetler

(57) ABSTRACT

A telescopic screw assembly for an injector includes an inner screw, an outer screw and a middle screw. The middle and outer screws are in a first threaded engagement, and the inner and middle screws are in a second threaded engagement. The inner screw is nested with the middle screw and the middle screw is nested with the outer screw in a contracted configuration of the screw assembly. Rotation of the outer screw in one direction advances the middle screw relative to the outer screw via the first threaded engagement and advances the inner screw relative to the middle screw via the second threaded engagement to telescopically extend the screw assembly into an expanded configuration. At least two of the inner, middle and outer screws are identified with (Continued)

a different visual indicator to enhance visual distinction between the screws, and readily visually indicate an extension progress of the screw assembly.

22 Claims, 5 Drawing Sheets

(52) U.S. Cl.
CPC ............... *F16H 25/2056* (2013.01); *A61M 2005/31508* (2013.01); *A61M 2005/31518* (2013.01); *A61M 2205/584* (2013.01)

(58) Field of Classification Search
CPC ......... A61M 2205/31508; A61M 2205/31518; A61M 2205/3152; A61M 2205/584; F16H 25/2056
See application file for complete search history.

(56) References Cited

U.S. PATENT DOCUMENTS

| | | | |
|---|---|---|---|
| 1,321,550 A | 11/1919 | Frank et al. | |
| 1,704,921 A | 3/1929 | Nicoll | |
| 1,795,530 A | 3/1931 | Cowan et al. | |
| 1,795,630 A * | 3/1931 | Wilson | B66F 13/00 254/1 |
| 2,453,590 A | 11/1948 | Poux | |
| 2,589,426 A | 3/1952 | Ogle | |
| 2,677,373 A | 5/1954 | Barradas | |
| 2,702,547 A | 2/1955 | Glass | |
| 2,860,635 A | 11/1958 | Wilburn | |
| 3,203,269 A | 8/1965 | Perrine | |
| 3,212,685 A | 10/1965 | Richard et al. | |
| 3,585,439 A | 6/1971 | Schneeberger | |
| 3,623,474 A | 11/1971 | Heilman et al. | |
| 3,705,582 A | 12/1972 | Stumpf et al. | |
| 3,708,945 A | 1/1973 | Klettke | |
| 3,794,028 A | 2/1974 | Mueller et al. | |
| 3,834,387 A | 9/1974 | Brown | |
| 3,994,295 A | 11/1976 | Wulff | |
| 4,085,747 A | 4/1978 | Lee | |
| 4,189,065 A | 2/1980 | Herold | |
| 4,195,636 A | 4/1980 | Behnke | |
| 4,218,724 A | 8/1980 | Kaufman | |
| 4,254,768 A | 3/1981 | Ty | |
| 4,273,122 A | 6/1981 | Whitney et al. | |
| 4,300,554 A | 11/1981 | Hessberg et al. | |
| 4,324,262 A | 4/1982 | Hall | |
| 4,403,987 A | 9/1983 | Gottinger | |
| 4,425,120 A | 1/1984 | Sampson et al. | |
| 4,435,173 A | 3/1984 | Siposs et al. | |
| 4,465,478 A | 8/1984 | Sabelman et al. | |
| 4,502,488 A | 3/1985 | Degironimo et al. | |
| 4,504,263 A | 3/1985 | Steuer et al. | |
| 4,549,554 A | 10/1985 | Markham | |
| 4,564,054 A | 1/1986 | Gustavsson | |
| 4,565,543 A | 1/1986 | Bekkering et al. | |
| 4,583,974 A | 4/1986 | Kokernak | |
| 4,585,439 A | 4/1986 | Michel | |
| 4,599,082 A | 7/1986 | Grimard | |
| 4,601,702 A | 7/1986 | Hudson | |
| 4,636,201 A | 1/1987 | Ambrose et al. | |
| 4,664,654 A | 5/1987 | Strauss | |
| 4,685,903 A | 8/1987 | Cable et al. | |
| 4,695,274 A | 9/1987 | Fox | |
| 4,698,055 A | 10/1987 | Sealfon | |
| 4,702,738 A | 10/1987 | Spencer | |
| 4,704,105 A | 11/1987 | Adorjan et al. | |
| 4,710,178 A | 12/1987 | Henri et al. | |
| 4,729,208 A | 3/1988 | Galy et al. | |
| 4,735,311 A | 4/1988 | Lowe et al. | |
| 4,737,144 A | 4/1988 | Choksi | |
| 4,772,272 A | 9/1988 | McFarland | |
| 4,810,215 A | 3/1989 | Kaneko | |
| 4,810,249 A | 3/1989 | Haber et al. | |
| 4,813,426 A | 3/1989 | Haber et al. | |
| 4,840,185 A | 6/1989 | Hernandez | |
| 4,850,966 A | 7/1989 | Grau et al. | |
| 4,861,341 A | 8/1989 | Woodburn | |
| 4,863,434 A | 9/1989 | Bayless | |
| 4,867,743 A | 9/1989 | Vaillancourt | |
| 4,874,383 A | 10/1989 | McNaughton | |
| 4,882,575 A | 11/1989 | Kawahara | |
| 4,886,499 A | 12/1989 | Cirelli et al. | |
| 4,892,521 A | 1/1990 | Laico et al. | |
| 4,897,083 A | 1/1990 | Martell | |
| 4,900,310 A | 2/1990 | Ogle, II | |
| 4,915,702 A | 4/1990 | Haber | |
| 4,919,569 A | 4/1990 | Wittenzellner | |
| 4,919,596 A | 4/1990 | Slate et al. | |
| 4,923,446 A | 5/1990 | Page et al. | |
| 4,929,241 A | 5/1990 | Kulli | |
| 4,950,241 A | 8/1990 | Ranford | |
| 4,950,246 A | 8/1990 | Muller | |
| 4,957,490 A | 9/1990 | Byrne et al. | |
| 4,964,866 A | 10/1990 | Szwarc | |
| 4,994,045 A | 2/1991 | Ranford | |
| 4,998,924 A | 3/1991 | Ranford | |
| 5,019,051 A | 5/1991 | Hake | |
| 5,051,109 A | 9/1991 | Simon | |
| 5,062,828 A | 11/1991 | Waltz | |
| D322,671 S | 12/1991 | Szwarc | |
| 5,088,988 A | 2/1992 | Talonn et al. | |
| 5,109,850 A | 5/1992 | Blanco et al. | |
| 5,112,317 A | 5/1992 | Michel | |
| 5,114,406 A | 5/1992 | Gabriel et al. | |
| 5,127,910 A | 7/1992 | Talonn et al. | |
| 5,131,816 A | 7/1992 | Brown et al. | |
| 5,147,326 A | 9/1992 | Talonn et al. | |
| 5,156,599 A | 10/1992 | Ranford et al. | |
| 5,190,521 A | 3/1993 | Hubbard et al. | |
| 5,217,437 A | 6/1993 | Talonn et al. | |
| 5,246,670 A | 9/1993 | Haber et al. | |
| 5,254,096 A | 10/1993 | Rondelet et al. | |
| 5,267,977 A | 12/1993 | Feeney, Jr. | |
| 5,269,762 A | 12/1993 | Armbruster et al. | |
| 5,275,582 A | 1/1994 | Wimmer | |
| 5,282,593 A * | 2/1994 | Fast | A47B 9/04 108/147 |
| 5,295,966 A | 3/1994 | Stern et al. | |
| 5,298,023 A | 3/1994 | Haber et al. | |
| 5,300,045 A | 4/1994 | Plassche, Jr. | |
| 5,318,522 A | 6/1994 | D'Antonio | |
| 5,338,311 A | 8/1994 | Mahurkar | |
| 5,342,313 A | 8/1994 | Campbell et al. | |
| 5,348,544 A | 9/1994 | Sweeney et al. | |
| 5,366,498 A | 11/1994 | Brannan et al. | |
| 5,376,785 A | 12/1994 | Chin et al. | |
| 5,383,865 A | 1/1995 | Michel | |
| D356,150 S | 3/1995 | Duggan et al. | |
| 5,415,645 A | 5/1995 | Friend et al. | |
| 5,456,360 A | 10/1995 | Griffin | |
| 5,478,315 A | 12/1995 | Brothers et al. | |
| 5,478,316 A | 12/1995 | Bitdinger et al. | |
| 5,482,446 A | 1/1996 | Williamson et al. | |
| 5,496,274 A | 3/1996 | Graves et al. | |
| 5,501,665 A | 3/1996 | Jhuboo et al. | |
| 5,505,709 A | 4/1996 | Funderburk et al. | |
| 5,562,624 A | 10/1996 | Righi et al. | |
| 5,562,686 A | 10/1996 | Sauer et al. | |
| 5,593,390 A | 1/1997 | Castellano et al. | |
| 5,609,580 A | 3/1997 | Kwiatkowski et al. | |
| 5,611,785 A | 3/1997 | Mito et al. | |
| 5,616,132 A | 4/1997 | Newman | |
| 5,624,400 A | 4/1997 | Firth et al. | |
| 5,637,095 A | 6/1997 | Nason et al. | |
| 5,643,218 A | 7/1997 | Lynn et al. | |
| 5,645,530 A | 7/1997 | Boukhny et al. | |
| 5,645,955 A | 7/1997 | Maglica | |
| 5,647,853 A | 7/1997 | Feldmann et al. | |
| 5,658,256 A | 8/1997 | Shields | |
| 5,662,678 A | 9/1997 | Macklin | |
| 5,672,160 A | 9/1997 | Osterlind et al. | |

(56) References Cited

U.S. PATENT DOCUMENTS

| | | | |
|---|---|---|---|
| 5,690,618 | A | 11/1997 | Smith et al. |
| 5,697,908 | A | 12/1997 | Imbert et al. |
| 5,697,916 | A | 12/1997 | Schraga |
| 5,725,500 | A | 3/1998 | Micheler |
| 5,728,075 | A | 3/1998 | Levander |
| D393,314 | S | 4/1998 | Meisner et al. |
| 5,741,275 | A | 4/1998 | Wyssmann |
| 5,766,186 | A | 6/1998 | Faraz et al. |
| 5,776,103 | A | 7/1998 | Kriesel et al. |
| 5,795,675 | A | 8/1998 | Maglica |
| 5,800,420 | A | 9/1998 | Gross et al. |
| 5,807,375 | A | 9/1998 | Gross et al. |
| 5,810,167 | A | 9/1998 | Fujii |
| 5,810,784 | A | 9/1998 | Tamaro |
| 5,814,020 | A | 9/1998 | Gross |
| 5,830,187 | A | 11/1998 | Kriesel et al. |
| 5,836,920 | A | 11/1998 | Robertson |
| 5,848,991 | A | 12/1998 | Gross et al. |
| 5,851,197 | A | 12/1998 | Marano et al. |
| 5,858,001 | A | 1/1999 | Tsais et al. |
| 5,858,008 | A | 1/1999 | Capaccio |
| 5,868,710 | A | 2/1999 | Battiato et al. |
| 5,893,842 | A | 4/1999 | Imbert |
| 5,894,015 | A | 4/1999 | Rechtin |
| 5,919,167 | A | 7/1999 | Mulhauser et al. |
| 5,926,596 | A | 7/1999 | Edwards et al. |
| 5,931,814 | A | 8/1999 | Alex et al. |
| 5,941,850 | A | 8/1999 | Shah et al. |
| 5,944,699 | A | 8/1999 | Barrelle et al. |
| 5,948,392 | A | 9/1999 | Haslwanter et al. |
| 5,954,697 | A | 9/1999 | Srisathapat et al. |
| 5,957,895 | A | 9/1999 | Sage et al. |
| 5,968,011 | A | 10/1999 | Larsen et al. |
| 5,989,221 | A | 11/1999 | Hjertman |
| 5,993,423 | A | 11/1999 | Choi |
| 6,004,296 | A | 12/1999 | Jansen et al. |
| 6,004,297 | A | 12/1999 | Steenfeldt-Jensen et al. |
| 6,033,245 | A | 3/2000 | Yamkovoy |
| 6,033,377 | A | 3/2000 | Rasmussen et al. |
| 6,045,533 | A | 4/2000 | Kriesel et al. |
| 6,064,797 | A | 5/2000 | Crittendon et al. |
| 6,074,369 | A | 6/2000 | Sage et al. |
| 6,162,197 | A | 12/2000 | Mohammad |
| 6,186,979 | B1 | 2/2001 | Dysarz |
| 6,186,982 | B1 | 2/2001 | Gross et al. |
| 6,189,292 | B1 | 2/2001 | Odell et al. |
| 6,200,289 | B1 | 3/2001 | Hochman et al. |
| 6,200,296 | B1 | 3/2001 | Dibiasi et al. |
| 6,224,569 | B1 | 5/2001 | Brimhall |
| 6,248,093 | B1 | 6/2001 | Moberg |
| 6,270,481 | B1 | 8/2001 | Mason et al. |
| 6,277,095 | B1 | 8/2001 | Kriesel et al. |
| 6,277,098 | B1 | 8/2001 | Klitmose et al. |
| 6,277,099 | B1 | 8/2001 | Strowe et al. |
| 6,287,283 | B1 | 9/2001 | Ljunggreen et al. |
| 6,293,925 | B1 | 9/2001 | Safabash et al. |
| 6,302,633 | B1 | 10/2001 | Poe |
| 6,336,729 | B1 | 1/2002 | Pavelle et al. |
| 6,345,968 | B1 | 2/2002 | Shupe |
| 6,377,848 | B1 | 4/2002 | Garde et al. |
| 6,391,005 | B1 | 5/2002 | Lum et al. |
| 6,423,029 | B1 | 7/2002 | Elsberry |
| D461,243 | S | 8/2002 | Niedospial |
| D465,026 | S | 10/2002 | May et al. |
| 6,458,102 | B1 | 10/2002 | Mann et al. |
| 6,485,461 | B1 | 11/2002 | Mason et al. |
| 6,485,465 | B2 | 11/2002 | Moberg et al. |
| 6,500,150 | B1 | 12/2002 | Gross et al. |
| 6,503,231 | B1 | 1/2003 | Prausnitz et al. |
| 6,511,336 | B1 | 1/2003 | Turek et al. |
| 6,517,517 | B1 | 2/2003 | Farrugia et al. |
| D471,274 | S | 3/2003 | Diaz et al. |
| D471,983 | S | 3/2003 | Hippolyte et al. |
| 6,554,800 | B1 | 4/2003 | Nezhadian et al. |
| 6,558,351 | B1 | 5/2003 | Steil et al. |
| 6,565,541 | B2 | 5/2003 | Sharp |
| 6,589,229 | B1 | 7/2003 | Connelly et al. |
| 6,595,956 | B1 | 7/2003 | Gross et al. |
| 6,595,960 | B2 | 7/2003 | West et al. |
| 6,645,181 | B1 | 11/2003 | Lavi et al. |
| 6,652,482 | B2 | 11/2003 | Hochman |
| 6,656,158 | B2 | 12/2003 | Mahoney et al. |
| 6,656,159 | B2 | 12/2003 | Flaherty |
| 6,659,980 | B2 | 12/2003 | Moberg et al. |
| 6,673,033 | B1 | 1/2004 | Sciulli et al. |
| 6,679,862 | B2 | 1/2004 | Diaz et al. |
| 6,685,678 | B2 | 2/2004 | Evans et al. |
| 6,689,118 | B2 | 2/2004 | Alchas et al. |
| 6,699,218 | B2 | 3/2004 | Flaherty et al. |
| 6,719,141 | B2 | 4/2004 | Heinz et al. |
| 6,722,916 | B2 | 4/2004 | Buccinna et al. |
| 6,743,211 | B1 | 6/2004 | Prausnitz et al. |
| 6,749,587 | B2 | 6/2004 | Flaherty |
| 6,752,783 | B2 | 6/2004 | Hung et al. |
| 6,752,787 | B1 | 6/2004 | Causey et al. |
| 6,767,336 | B1 | 7/2004 | Kaplan |
| 6,768,425 | B2 | 7/2004 | Flaherty et al. |
| 6,786,890 | B2 | 9/2004 | Preuthun et al. |
| 6,800,071 | B1 | 10/2004 | McConnell et al. |
| 6,805,687 | B2 | 10/2004 | Dextradeur et al. |
| 6,824,529 | B2 | 11/2004 | Gross et al. |
| 6,843,782 | B2 | 1/2005 | Gross et al. |
| 6,854,620 | B2 | 2/2005 | Ramey |
| 6,905,298 | B1 | 6/2005 | Haring |
| 6,907,679 | B2 | 6/2005 | Yarborough et al. |
| 6,908,452 | B2 | 6/2005 | Diaz et al. |
| 6,960,192 | B1 | 11/2005 | Flaherty et al. |
| 6,979,316 | B1 | 12/2005 | Rubin et al. |
| 6,997,727 | B1 | 2/2006 | Legrady et al. |
| 7,001,360 | B2 | 2/2006 | Veasey et al. |
| 7,004,104 | B1 * | 2/2006 | Kundus ............... G09F 17/00 116/173 |
| 7,004,929 | B2 | 2/2006 | McWethy et al. |
| 7,025,226 | B2 | 4/2006 | Ramey |
| 7,033,338 | B2 | 4/2006 | Vilks et al. |
| 7,034,223 | B2 | 4/2006 | Fan et al. |
| 7,048,715 | B2 | 5/2006 | Diaz et al. |
| 7,060,054 | B2 | 6/2006 | Nissels |
| 7,060,059 | B2 | 6/2006 | Keith et al. |
| 7,066,909 | B1 | 6/2006 | Peter et al. |
| 7,094,221 | B2 | 8/2006 | Veasey et al. |
| 7,097,637 | B2 | 8/2006 | Triplett et al. |
| 7,112,187 | B2 | 9/2006 | Karlsson |
| 7,128,727 | B2 | 10/2006 | Flaherty et al. |
| 7,144,384 | B2 | 12/2006 | Gorman et al. |
| D544,092 | S | 6/2007 | Lewis |
| 7,225,694 | B2 | 6/2007 | Said |
| 7,247,149 | B2 | 7/2007 | Beyerlein |
| 7,250,037 | B2 | 7/2007 | Shermer et al. |
| 7,267,669 | B2 | 9/2007 | Staunton et al. |
| RE39,923 | E | 11/2007 | Blom |
| 7,291,132 | B2 | 11/2007 | DeRuntz et al. |
| 7,291,159 | B2 | 11/2007 | Schmelzeisen-Redeker et al. |
| 7,303,549 | B2 | 12/2007 | Flaherty et al. |
| 7,326,194 | B2 | 2/2008 | Zinger et al. |
| 7,344,385 | B2 | 3/2008 | Chen |
| 7,364,570 | B2 | 4/2008 | Gerondale et al. |
| 7,377,912 | B2 | 5/2008 | Graf et al. |
| 7,390,312 | B2 | 6/2008 | Barrelle |
| 7,390,314 | B2 | 6/2008 | Stutz et al. |
| 7,407,493 | B2 | 8/2008 | Cane' |
| 7,418,880 | B2 | 9/2008 | Smith |
| D578,210 | S | 10/2008 | Muta et al. |
| 7,442,186 | B2 | 10/2008 | Blomquist |
| 7,455,663 | B2 | 11/2008 | Bikovsky |
| 7,465,290 | B2 | 12/2008 | Reilly |
| 7,468,055 | B2 | 12/2008 | Prais et al. |
| 7,488,181 | B2 | 2/2009 | van Haaster |
| 7,497,842 | B2 | 3/2009 | Diaz et al. |
| 7,500,963 | B2 | 3/2009 | Westbye et al. |
| 7,501,587 | B2 | 3/2009 | English |
| 7,503,786 | B2 | 3/2009 | Kato et al. |
| 7,530,964 | B2 | 5/2009 | Lavi et al. |
| 7,540,858 | B2 | 6/2009 | DiBiasi |

(56) References Cited

U.S. PATENT DOCUMENTS

| | | |
|---|---|---|
| 7,547,281 B2 | 6/2009 | Hayes et al. |
| 7,565,208 B2 | 7/2009 | Harris et al. |
| 7,569,050 B2 | 8/2009 | Moberg et al. |
| D600,341 S | 9/2009 | Loerwald |
| 7,585,287 B2 | 9/2009 | Bresina et al. |
| 7,588,559 B2 | 9/2009 | Aravena et al. |
| 7,589,974 B2 | 9/2009 | Grady et al. |
| D602,155 S | 10/2009 | Foley et al. |
| D602,586 S | 10/2009 | Foley et al. |
| D604,835 S | 11/2009 | Conley |
| 7,611,491 B2 | 11/2009 | Pickhard |
| 7,628,770 B2 | 12/2009 | Ethelfeld |
| 7,628,772 B2 | 12/2009 | Mcconnell et al. |
| 7,628,782 B2 | 12/2009 | Adair et al. |
| 7,637,891 B2 | 12/2009 | Wall |
| 7,637,899 B2 | 12/2009 | Woolston et al. |
| 7,641,649 B2 | 1/2010 | Moberg et al. |
| 7,660,627 B2 | 2/2010 | Mcnichols et al. |
| 7,678,079 B2 | 3/2010 | Shermer et al. |
| 7,682,338 B2 | 3/2010 | Griffin |
| 7,686,787 B2 | 3/2010 | Moberg et al. |
| 7,699,829 B2 | 4/2010 | Harris et al. |
| 7,699,833 B2 | 4/2010 | Moberg et al. |
| 7,704,088 B2 | 4/2010 | Sakamoto |
| 7,704,227 B2 | 4/2010 | Moberg et al. |
| 7,704,229 B2 | 4/2010 | Moberg et al. |
| 7,704,231 B2 | 4/2010 | Pongpairochana et al. |
| 7,708,717 B2 | 5/2010 | Estes et al. |
| 7,713,238 B2 | 5/2010 | Mernoe |
| 7,713,240 B2 | 5/2010 | Istoc et al. |
| 7,717,903 B2 | 5/2010 | Estes et al. |
| 7,717,913 B2 | 5/2010 | Novak et al. |
| 7,722,574 B2 | 5/2010 | Toman et al. |
| 7,736,333 B2 | 6/2010 | Gillespie, III |
| 7,736,344 B2 | 6/2010 | Moberg et al. |
| 7,744,589 B2 | 6/2010 | Mounce et al. |
| 7,749,194 B2 | 7/2010 | Edwards et al. |
| 7,758,548 B2 | 7/2010 | Gillespie et al. |
| 7,758,550 B2 | 7/2010 | Bollenbach et al. |
| 7,766,867 B2 | 8/2010 | Lynch et al. |
| 7,776,030 B2 | 8/2010 | Estes et al. |
| 7,780,637 B2 | 8/2010 | Jerde et al. |
| 7,789,857 B2 | 9/2010 | Moberg et al. |
| 7,794,426 B2 | 9/2010 | Briones et al. |
| 7,794,427 B2 | 9/2010 | Estes et al. |
| 7,801,599 B2 | 9/2010 | Young et al. |
| 7,806,868 B2 | 10/2010 | De et al. |
| 7,828,528 B2 | 11/2010 | Estes et al. |
| 7,837,659 B2 | 11/2010 | Bush et al. |
| 7,846,132 B2 | 12/2010 | Gravesen et al. |
| 7,854,723 B2 | 12/2010 | Hwang et al. |
| 7,857,131 B2 | 12/2010 | Vedrine |
| 7,879,025 B2 | 2/2011 | Jacobson et al. |
| 7,901,382 B2 | 3/2011 | Daily et al. |
| 7,905,867 B2 | 3/2011 | Veasey et al. |
| 7,918,825 B2 | 4/2011 | O'Connor et al. |
| 7,935,104 B2 | 5/2011 | Yodat et al. |
| 7,935,105 B2 | 5/2011 | Miller et al. |
| 7,938,803 B2 | 5/2011 | Mernoe et al. |
| 7,955,305 B2 | 6/2011 | Moberg et al. |
| 7,967,784 B2 | 6/2011 | Pongpairochana et al. |
| 7,967,795 B1 | 6/2011 | Cabiri |
| 7,976,514 B2 | 7/2011 | Abry et al. |
| 7,981,105 B2 | 7/2011 | Adair et al. |
| 3,002,754 A1 | 8/2011 | Kawamura et al. |
| 7,988,683 B2 | 8/2011 | Adair et al. |
| 7,993,300 B2 | 8/2011 | Nyholm et al. |
| 7,993,301 B2 | 8/2011 | Boyd et al. |
| 7,998,111 B2 | 8/2011 | Moberg et al. |
| 8,021,357 B2 | 9/2011 | Tanaka et al. |
| 8,025,658 B2 | 9/2011 | Chong et al. |
| 8,029,469 B2 | 10/2011 | Ethelfeld |
| 8,034,019 B2 | 10/2011 | Nair et al. |
| 8,038,666 B2 | 10/2011 | Triplett et al. |
| 8,057,431 B2 | 11/2011 | Woehr et al. |
| 8,057,436 B2 | 11/2011 | Causey et al. |
| 8,062,253 B2 | 11/2011 | Nielsen et al. |
| 8,062,255 B2 | 11/2011 | Brunnberg et al. |
| 8,066,694 B2 | 11/2011 | Wagener |
| D650,079 S | 12/2011 | Presta et al. |
| D650,903 S | 12/2011 | Kosinski et al. |
| 8,086,306 B2 | 12/2011 | Katzman et al. |
| D652,503 S | 1/2012 | Cameron et al. |
| 8,105,279 B2 | 1/2012 | Mernoe et al. |
| 8,105,293 B2 | 1/2012 | Pickhard |
| 8,114,046 B2 | 2/2012 | Covino et al. |
| 8,114,064 B2 | 2/2012 | Alferness et al. |
| 8,114,066 B2 | 2/2012 | Naef et al. |
| 8,118,781 B2 | 2/2012 | Knopper et al. |
| 8,121,603 B2 | 2/2012 | Zhi |
| D657,462 S | 4/2012 | Siroky |
| 8,147,446 B2 | 4/2012 | Yodfat et al. |
| 8,151,169 B2 | 4/2012 | Bieth et al. |
| 8,152,764 B2 | 4/2012 | Istoc et al. |
| 8,152,770 B2 | 4/2012 | Reid |
| 8,152,779 B2 | 4/2012 | Cabiri |
| 8,152,793 B2 | 4/2012 | Keinaenen et al. |
| 8,157,693 B2 | 4/2012 | Waksmundzki |
| 8,157,769 B2 | 4/2012 | Cabiri |
| 8,162,674 B2 | 4/2012 | Cho et al. |
| 8,162,923 B2 | 4/2012 | Adams et al. |
| 8,167,841 B2 | 5/2012 | Teisen-Simony et al. |
| 8,172,591 B2 | 5/2012 | Wertz |
| 8,172,804 B2 | 5/2012 | Bikovsky |
| 8,177,749 B2 | 5/2012 | Slate et al. |
| 8,182,462 B2 | 5/2012 | Istoc et al. |
| 8,197,444 B1 | 6/2012 | Bazargan et al. |
| 8,206,351 B2 | 6/2012 | Sugimoto et al. |
| 8,221,356 B2 | 7/2012 | Enggaard et al. |
| 8,267,921 B2 | 9/2012 | Yodfat et al. |
| 8,287,520 B2 | 10/2012 | Drew et al. |
| 8,292,647 B1 | 10/2012 | Mcgrath et al. |
| 8,308,679 B2 | 11/2012 | Hanson et al. |
| 8,308,695 B2 | 11/2012 | Laiosa |
| 8,323,250 B2 | 12/2012 | Chong et al. |
| 8,348,898 B2 | 1/2013 | Cabiri |
| 8,366,668 B2 | 2/2013 | Maritan |
| 8,372,039 B2 | 2/2013 | Mernoe et al. |
| 8,373,421 B2 | 2/2013 | Lindegger et al. |
| 8,409,141 B2 | 4/2013 | Johansen et al. |
| 8,409,142 B2 | 4/2013 | Causey et al. |
| 8,409,143 B2 | 4/2013 | Lanigan et al. |
| 8,409,149 B2 | 4/2013 | Hommann et al. |
| 8,414,533 B2 | 4/2013 | Alexandersson |
| 8,414,557 B2 | 4/2013 | Istoc et al. |
| 8,425,468 B2 | 4/2013 | Weston |
| 8,430,847 B2 | 4/2013 | Mernoe et al. |
| 8,465,455 B2 | 6/2013 | Cabiri |
| 8,469,942 B2 | 6/2013 | Kow et al. |
| 8,474,332 B2 | 7/2013 | Bente et al. |
| 8,475,408 B2 | 7/2013 | Mernoe et al. |
| 8,479,595 B2 | 7/2013 | Vazquez et al. |
| 8,490,790 B2 | 7/2013 | Cocheteux et al. |
| 8,495,918 B2 | 7/2013 | Bazargan et al. |
| 8,496,862 B2 | 7/2013 | Zelkovich et al. |
| 8,512,287 B2 | 8/2013 | Cindrich et al. |
| 8,512,295 B2 | 8/2013 | Evans et al. |
| 8,517,987 B2 | 8/2013 | Istoc et al. |
| 8,517,992 B2 | 8/2013 | Jones |
| 8,523,803 B1 | 9/2013 | Favreau |
| 8,551,046 B2 | 10/2013 | Causey et al. |
| 8,556,856 B2 | 10/2013 | Bazargan et al. |
| 8,562,364 B2 | 10/2013 | Lin et al. |
| 8,568,361 B2 | 10/2013 | Yodfat et al. |
| 8,574,216 B2 | 11/2013 | Istoc et al. |
| 8,603,026 B2 | 12/2013 | Favreau |
| 8,603,027 B2 | 12/2013 | Favreau |
| 8,603,028 B2 | 12/2013 | Mudd et al. |
| 8,622,966 B2 | 1/2014 | Causey et al. |
| 8,628,510 B2 | 1/2014 | Bazargan et al. |
| 8,647,303 B2 | 2/2014 | Cowe |
| 8,674,288 B2 | 3/2014 | Hanson et al. |
| 8,679,060 B2 | 3/2014 | Mernoe et al. |
| D702,834 S | 4/2014 | Norton et al. |

(56) References Cited

U.S. PATENT DOCUMENTS

| | | |
|---|---|---|
| 8,690,855 B2 | 4/2014 | Alderete et al. |
| 8,708,961 B2 | 4/2014 | Field et al. |
| 8,721,603 B2 | 5/2014 | Lundquist |
| 8,751,237 B2 | 6/2014 | Kubota |
| 8,753,326 B2 | 6/2014 | Chong et al. |
| 8,753,331 B2 | 6/2014 | Murphy |
| 8,764,707 B2 | 7/2014 | Moberg et al. |
| 8,764,723 B2 | 7/2014 | Chong et al. |
| 8,771,222 B2 | 7/2014 | Kanderian et al. |
| 8,777,896 B2 | 7/2014 | Starkweather et al. |
| 8,777,924 B2 | 7/2014 | Kanderian et al. |
| 8,777,925 B2 | 7/2014 | Patton |
| 8,784,369 B2 | 7/2014 | Starkweather et al. |
| 8,784,370 B2 | 7/2014 | Lebel et al. |
| 8,784,378 B2 | 7/2014 | Weinandy |
| 8,790,295 B1 | 7/2014 | Sigg et al. |
| 8,795,224 B2 | 8/2014 | Starkweather et al. |
| 8,795,231 B2 | 8/2014 | Chong et al. |
| 8,795,260 B2 | 8/2014 | Drew |
| 8,801,668 B2 | 8/2014 | Ali et al. |
| 8,801,679 B2 | 8/2014 | Iio et al. |
| 8,810,394 B2 | 8/2014 | Kalpin |
| 8,814,379 B2 | 8/2014 | Griffiths et al. |
| 8,858,508 B2 | 10/2014 | Lavi et al. |
| 8,876,778 B2 | 11/2014 | Carrel |
| 8,911,410 B2 | 12/2014 | Ekman et al. |
| 8,915,882 B2 | 12/2014 | Cabiri |
| 8,915,886 B2 | 12/2014 | Cowe |
| 8,920,374 B2 | 12/2014 | Bokelman et al. |
| 8,932,266 B2 | 1/2015 | Wozencroft |
| 8,979,802 B2 | 3/2015 | Woehr |
| 8,986,250 B2 | 3/2015 | Beebe et al. |
| 9,011,164 B2 | 4/2015 | Filman et al. |
| 9,011,387 B2 | 4/2015 | Ekman et al. |
| 9,061,104 B2 | 6/2015 | Daniel |
| 9,061,110 B2 | 6/2015 | Avery et al. |
| 9,072,827 B2 | 7/2015 | Cabiri |
| 9,072,845 B2 | 7/2015 | Hiles |
| 9,089,475 B2 | 7/2015 | Fangrow |
| 9,089,641 B2 | 7/2015 | Kavazov |
| 9,138,534 B2 | 9/2015 | Yodfat et al. |
| 9,149,575 B2 | 10/2015 | Cabiri |
| 9,173,997 B2 | 11/2015 | Gross et al. |
| 9,180,248 B2 | 11/2015 | Moberg et al. |
| 9,205,199 B2 | 12/2015 | Kemp et al. |
| D747,799 S | 1/2016 | Norton et al. |
| 9,233,215 B2 | 1/2016 | Hourmand et al. |
| 9,259,532 B2 | 2/2016 | Cabiri |
| 9,283,327 B2 | 3/2016 | Hourmand et al. |
| 9,308,327 B2 | 4/2016 | Marshall et al. |
| 9,314,569 B2 | 4/2016 | Causey et al. |
| 9,320,849 B2 | 4/2016 | Smith et al. |
| 9,345,834 B2 | 5/2016 | Henley et al. |
| 9,345,836 B2 | 5/2016 | Cabiri et al. |
| 9,350,634 B2 | 5/2016 | Fadell |
| 9,352,090 B2 | 5/2016 | Brereton et al. |
| 9,364,606 B2 | 6/2016 | Cindrich et al. |
| 9,381,300 B2 | 7/2016 | Smith et al. |
| 9,393,365 B2 | 7/2016 | Cabiri |
| 9,421,323 B2 | 8/2016 | Cabiri et al. |
| 9,421,337 B2 | 8/2016 | Kemp et al. |
| 9,427,531 B2 | 8/2016 | Hourmand et al. |
| 9,446,196 B2 | 9/2016 | Hourmand et al. |
| 9,452,261 B2 | 9/2016 | Alon |
| 9,463,280 B2 | 10/2016 | Cabiri |
| 9,463,889 B2 | 10/2016 | Schmitz et al. |
| 9,468,720 B2 | 10/2016 | Mudd et al. |
| 9,474,859 B2 | 10/2016 | Ekman et al. |
| 9,492,622 B2 | 11/2016 | Brereton et al. |
| 9,522,234 B2 | 12/2016 | Cabiri |
| 9,539,384 B2 | 1/2017 | Servansky |
| 9,539,388 B2 | 1/2017 | Causey et al. |
| 9,539,757 B2 | 1/2017 | Ramirez et al. |
| 9,572,926 B2 | 2/2017 | Cabiri |
| 9,572,927 B2 | 2/2017 | Bruggemann et al. |
| 9,579,471 B2 | 2/2017 | Carrel et al. |
| 9,610,407 B2 | 4/2017 | Bruggemann et al. |
| 9,656,019 B2 | 5/2017 | Cabiri et al. |
| 9,656,021 B2 | 5/2017 | Brereton et al. |
| 9,656,025 B2 | 5/2017 | Bostrom et al. |
| 9,707,356 B2 | 7/2017 | Hourmand et al. |
| 9,744,306 B2 | 8/2017 | Cowe |
| 9,775,948 B2 | 10/2017 | Bechmann et al. |
| 9,782,545 B2 | 10/2017 | Gross et al. |
| 9,789,247 B2 | 10/2017 | Kamen et al. |
| 9,814,830 B2 | 11/2017 | Mernoe et al. |
| 9,814,839 B2 | 11/2017 | Eaton |
| 9,849,242 B2 | 12/2017 | Henley et al. |
| 9,862,519 B2 | 1/2018 | Deutschle et al. |
| 9,999,722 B2 | 6/2018 | Yodfat et al. |
| 10,010,681 B2 | 7/2018 | Koch et al. |
| 10,076,356 B2 | 9/2018 | Hadvary et al. |
| 10,143,794 B2 | 12/2018 | Lanigan et al. |
| 10,149,943 B2 | 12/2018 | Bar-El et al. |
| D838,367 S | 1/2019 | Norton et al. |
| 10,166,335 B2 | 1/2019 | Reber et al. |
| 10,207,051 B2 | 2/2019 | Cereda et al. |
| 10,227,161 B2 | 3/2019 | Auerbach |
| 10,232,116 B2 | 3/2019 | Ekman et al. |
| 10,258,740 B2 | 4/2019 | McLoughlin et al. |
| 10,376,641 B2 | 8/2019 | Hirschel et al. |
| 10,376,647 B2 | 8/2019 | Farris et al. |
| 10,434,262 B2 | 10/2019 | Bendek et al. |
| 10,576,213 B2 | 3/2020 | Gylleby |
| 10,576,220 B2 | 3/2020 | Armes |
| 10,583,260 B2 | 3/2020 | Kemp |
| 10,603,430 B2 | 3/2020 | Shor et al. |
| 10,722,645 B2 | 7/2020 | Kamen et al. |
| 10,842,942 B2 | 11/2020 | Iibuchi et al. |
| 2001/0005781 A1 | 6/2001 | Bergens et al. |
| 2001/0018937 A1 | 9/2001 | Nemoto |
| 2001/0025168 A1 | 9/2001 | Gross et al. |
| 2001/0034502 A1 | 10/2001 | Moberg et al. |
| 2001/0041869 A1 | 11/2001 | Causey et al. |
| 2002/0010423 A1 | 1/2002 | Gross et al. |
| 2002/0016569 A1 | 2/2002 | Critchlow et al. |
| 2002/0029018 A1 | 3/2002 | Jeffrey |
| 2002/0040208 A1 | 4/2002 | Flaherty et al. |
| 2002/0055711 A1 | 5/2002 | Lavi et al. |
| 2002/0055718 A1 | 5/2002 | Hunt |
| 2002/0065488 A1 | 5/2002 | Suzuki et al. |
| 2002/0107487 A1 | 8/2002 | Preuthun |
| 2002/0120186 A1 | 8/2002 | Keimel |
| 2002/0123740 A1 | 9/2002 | Flaherty et al. |
| 2002/0151855 A1 | 10/2002 | Douglas et al. |
| 2002/0161332 A1 | 10/2002 | Ramey |
| 2002/0169215 A1 | 11/2002 | Meng |
| 2003/0009133 A1 | 1/2003 | Ramey |
| 2003/0014018 A1 | 1/2003 | Giambattista et al. |
| 2003/0050602 A1 | 3/2003 | Pettis et al. |
| 2003/0069518 A1 | 4/2003 | Daley et al. |
| 2003/0125671 A1 | 7/2003 | Aramata et al. |
| 2003/0135159 A1 | 7/2003 | Daily et al. |
| 2003/0160683 A1 | 8/2003 | Blomquist |
| 2003/0167039 A1 | 9/2003 | Moberg |
| 2003/0171717 A1 | 9/2003 | Farrugia et al. |
| 2003/0199825 A1 | 10/2003 | Flaherty et al. |
| 2003/0216683 A1 | 11/2003 | Shekalim |
| 2003/0236498 A1 | 12/2003 | Gross et al. |
| 2004/0000818 A1* | 1/2004 | Preuthun .......... A61M 5/14566 |
| | | 310/83 |
| 2004/0010207 A1 | 1/2004 | Flaherty et al. |
| 2004/0049160 A1 | 3/2004 | Hsieh et al. |
| 2004/0049161 A1 | 3/2004 | Sheam |
| 2004/0082911 A1 | 4/2004 | Tiu et al. |
| 2004/0092873 A1 | 5/2004 | Moberg |
| 2004/0116866 A1 | 6/2004 | Gorman et al. |
| 2004/0122359 A1 | 6/2004 | Wenz et al. |
| 2004/0122369 A1 | 6/2004 | Schriver et al. |
| 2004/0127857 A1 | 7/2004 | Shemesh et al. |
| 2004/0135078 A1 | 7/2004 | Mandro et al. |
| 2004/0158172 A1 | 8/2004 | Hancock |
| 2004/0158205 A1 | 8/2004 | Savage |
| 2004/0186419 A1 | 9/2004 | Cho |

(56) References Cited

U.S. PATENT DOCUMENTS

| | | |
|---|---|---|
| 2004/0186441 A1 | 9/2004 | Graf et al. |
| 2004/0210196 A1 | 10/2004 | Bush, Jr. et al. |
| 2004/0260233 A1 | 12/2004 | Garibotto et al. |
| 2005/0027255 A1 | 2/2005 | Lavi et al. |
| 2005/0033234 A1 | 2/2005 | Sadowski et al. |
| 2005/0038391 A1 | 2/2005 | Wittland et al. |
| 2005/0065466 A1 | 3/2005 | Vedrine |
| 2005/0065472 A1 | 3/2005 | Cindrich et al. |
| 2005/0071487 A1 | 3/2005 | Lu et al. |
| 2005/0113761 A1 | 5/2005 | Faust et al. |
| 2005/0124940 A1 | 6/2005 | Martin et al. |
| 2005/0154353 A1 | 7/2005 | Alheidt |
| 2005/0159706 A1 | 7/2005 | Wilkinson et al. |
| 2005/0171476 A1 | 8/2005 | Judson et al. |
| 2005/0171512 A1 | 8/2005 | Flaherty |
| 2005/0177136 A1 | 8/2005 | Miller |
| 2005/0197650 A1 | 9/2005 | Sugimoto et al. |
| 2005/0203461 A1 | 9/2005 | Flaherty et al. |
| 2005/0238507 A1 | 10/2005 | Diianni et al. |
| 2005/0245956 A1 | 11/2005 | Steinemann et al. |
| 2005/0283114 A1 | 12/2005 | Bresina et al. |
| 2006/0013716 A1 | 1/2006 | Nason et al. |
| 2006/0030816 A1 | 2/2006 | Zubry |
| 2006/0036216 A1 | 2/2006 | Rimlinger et al. |
| 2006/0095010 A1 | 5/2006 | Westbye |
| 2006/0095014 A1 | 5/2006 | Ethelfeld |
| 2006/0122577 A1 | 6/2006 | Poulsen et al. |
| 2006/0124269 A1 | 6/2006 | Miyazaki et al. |
| 2006/0173406 A1 | 8/2006 | Hayes et al. |
| 2006/0173439 A1 | 8/2006 | Thorne et al. |
| 2006/0184154 A1 | 8/2006 | Moberg et al. |
| 2006/0195029 A1 | 8/2006 | Shults et al. |
| 2006/0206054 A1 | 9/2006 | Shekalim |
| 2006/0206057 A1 | 9/2006 | Deruntz et al. |
| 2006/0211982 A1 | 9/2006 | Prestrelski et al. |
| 2006/0229569 A1 | 10/2006 | Lavi et al. |
| 2006/0264888 A1 | 11/2006 | Moberg et al. |
| 2006/0264889 A1 | 11/2006 | Moberg et al. |
| 2006/0264890 A1 | 11/2006 | Moberg et al. |
| 2006/0264894 A1 | 11/2006 | Moberg et al. |
| 2006/0270987 A1 | 11/2006 | Peter |
| 2006/0283465 A1 | 12/2006 | Nickel et al. |
| 2006/0293722 A1 | 12/2006 | Slatkine et al. |
| 2007/0021733 A1 | 1/2007 | Hansen et al. |
| 2007/0025879 A1 | 2/2007 | Vandergaw |
| 2007/0049865 A1 | 3/2007 | Radmer et al. |
| 2007/0073228 A1 | 3/2007 | Mernoe et al. |
| 2007/0079894 A1 | 4/2007 | Kraus et al. |
| 2007/0118405 A1 | 5/2007 | Campbell et al. |
| 2007/0167912 A1 | 7/2007 | Causey et al. |
| 2007/0179444 A1 | 8/2007 | Causey et al. |
| 2007/0185449 A1 | 8/2007 | Mernoe |
| 2007/0197954 A1 | 8/2007 | Keenan |
| 2007/0197968 A1 | 8/2007 | Pongpairochana et al. |
| 2007/0203454 A1 | 8/2007 | Shermer et al. |
| 2007/0233038 A1 | 10/2007 | Pruitt et al. |
| 2007/0265568 A1 | 11/2007 | Tsais et al. |
| 2007/0282269 A1 | 12/2007 | Carter et al. |
| 2008/0021439 A1 | 1/2008 | Brittingham et al. |
| 2008/0033367 A1 | 2/2008 | Haury et al. |
| 2008/0033369 A1 | 2/2008 | Kohlbrenner et al. |
| 2008/0033393 A1 | 2/2008 | Edwards et al. |
| 2008/0051711 A1 | 2/2008 | Mounce et al. |
| 2008/0051730 A1 | 2/2008 | Bikovsky |
| 2008/0059133 A1 | 3/2008 | Edwards et al. |
| 2008/0097326 A1 | 4/2008 | Moberg et al. |
| 2008/0097381 A1 | 4/2008 | Moberg et al. |
| 2008/0097387 A1 | 4/2008 | Spector |
| 2008/0108951 A1 | 5/2008 | Jerde et al. |
| 2008/0140006 A1 | 6/2008 | Eskuri et al. |
| 2008/0140014 A1 | 6/2008 | Miller et al. |
| 2008/0140018 A1 | 6/2008 | Enggaard et al. |
| 2008/0147004 A1 | 6/2008 | Mann et al. |
| 2008/0167641 A1 | 7/2008 | Hansen et al. |
| 2008/0188813 A1 | 8/2008 | Miller et al. |
| 2008/0208138 A1 | 8/2008 | Lim et al. |
| 2008/0215006 A1 | 9/2008 | Thorkild |
| 2008/0215013 A1 | 9/2008 | Felix-Faure |
| 2008/0215015 A1 | 9/2008 | Cindrich et al. |
| 2008/0243087 A1 | 10/2008 | Enggaard et al. |
| 2008/0249473 A1 | 10/2008 | Rutti et al. |
| 2008/0262436 A1 | 10/2008 | Olson |
| 2008/0269687 A1 | 10/2008 | Chong et al. |
| 2008/0269723 A1 | 10/2008 | Mastrototaro et al. |
| 2008/0274630 A1 | 11/2008 | Shelton et al. |
| 2008/0294143 A1 | 11/2008 | Tanaka et al. |
| 2008/0306449 A1 | 12/2008 | Kristensen et al. |
| 2008/0312601 A1 | 12/2008 | Cane |
| 2008/0319383 A1 | 12/2008 | Byland et al. |
| 2008/0319416 A1 | 12/2008 | Yodfat et al. |
| 2009/0012478 A1 | 1/2009 | Weston |
| 2009/0041805 A1 | 2/2009 | Walker |
| 2009/0048347 A1 | 2/2009 | Cohen et al. |
| 2009/0054750 A1 | 2/2009 | Jennewine |
| 2009/0069784 A1 | 3/2009 | Estes et al. |
| 2009/0076383 A1 | 3/2009 | Toews et al. |
| 2009/0076453 A1 | 3/2009 | Mejlhede et al. |
| 2009/0088694 A1 | 4/2009 | Carter et al. |
| 2009/0088731 A1 | 4/2009 | Campbell et al. |
| 2009/0093763 A1 | 4/2009 | Gonnelli et al. |
| 2009/0093792 A1 | 4/2009 | Gross et al. |
| 2009/0093793 A1 | 4/2009 | Gross et al. |
| 2009/0105650 A1 | 4/2009 | Wiegel et al. |
| 2009/0105663 A1 | 4/2009 | Brand et al. |
| 2009/0124977 A1 | 5/2009 | Jensen |
| 2009/0143730 A1 | 6/2009 | De Polo et al. |
| 2009/0143735 A1 | 6/2009 | De et al. |
| 2009/0149830 A1 | 6/2009 | Spector |
| 2009/0182277 A1 | 7/2009 | Carter |
| 2009/0182284 A1 | 7/2009 | Morgan |
| 2009/0204076 A1 | 8/2009 | Liversidge |
| 2009/0209896 A1 | 8/2009 | Selevan |
| 2009/0234319 A1 | 9/2009 | Marksteiner |
| 2009/0240240 A1 | 9/2009 | Hines et al. |
| 2009/0253973 A1 | 10/2009 | Bashan et al. |
| 2009/0259176 A1 | 10/2009 | Yairi |
| 2009/0281585 A1 | 11/2009 | Katzman et al. |
| 2009/0299288 A1 | 12/2009 | Sie et al. |
| 2009/0299290 A1 | 12/2009 | Moberg |
| 2009/0299397 A1 | 12/2009 | Ruan et al. |
| 2009/0326459 A1 | 12/2009 | Shipway et al. |
| 2009/0326509 A1 | 12/2009 | Muse et al. |
| 2010/0010455 A1 | 1/2010 | Elahi et al. |
| 2010/0018334 A1* | 1/2010 | Lessing ............... F16H 25/2056 74/89.35 |
| 2010/0030156 A1 | 2/2010 | Beebe et al. |
| 2010/0030198 A1 | 2/2010 | Beebe et al. |
| 2010/0049128 A1 | 2/2010 | Mckenzie et al. |
| 2010/0049144 A1 | 2/2010 | Mcconnell et al. |
| 2010/0057057 A1 | 3/2010 | Hayter et al. |
| 2010/0076382 A1 | 3/2010 | Weston |
| 2010/0076412 A1 | 3/2010 | Rush et al. |
| 2010/0094255 A1 | 4/2010 | Nycz et al. |
| 2010/0100076 A1 | 4/2010 | Rush et al. |
| 2010/0100077 A1 | 4/2010 | Rush et al. |
| 2010/0106098 A1 | 4/2010 | Atterbury et al. |
| 2010/0121314 A1 | 5/2010 | Iobbi |
| 2010/0137790 A1 | 6/2010 | Yodfat |
| 2010/0137831 A1 | 6/2010 | Tsals |
| 2010/0145303 A1 | 6/2010 | Yodfat et al. |
| 2010/0145305 A1 | 6/2010 | Alon |
| 2010/0160894 A1 | 6/2010 | Julian et al. |
| 2010/0162548 A1 | 7/2010 | Leidig |
| 2010/0168607 A1 | 7/2010 | Miesel |
| 2010/0168683 A1 | 7/2010 | Cabiri |
| 2010/0198157 A1 | 8/2010 | Gyrn et al. |
| 2010/0204657 A1 | 8/2010 | Yodfat et al. |
| 2010/0234767 A1 | 9/2010 | Sarstedt |
| 2010/0234830 A1 | 9/2010 | Straessler et al. |
| 2010/0241065 A1 | 9/2010 | Moberg et al. |
| 2010/0256486 A1 | 10/2010 | Savage |
| 2010/0264931 A1 | 10/2010 | Lindegger et al. |
| 2010/0268169 A1 | 10/2010 | Llewellyn-Hyde et al. |
| 2010/0274112 A1 | 10/2010 | Hoss et al. |

(56) References Cited

U.S. PATENT DOCUMENTS

| | | |
|---|---|---|
| 2010/0274192 A1 | 10/2010 | Mernoe |
| 2010/0280499 A1 | 11/2010 | Yodfat et al. |
| 2010/0331826 A1 | 12/2010 | Field et al. |
| 2011/0034900 A1 | 2/2011 | Yodfat et al. |
| 2011/0054399 A1 | 3/2011 | Chong et al. |
| 2011/0054400 A1 | 3/2011 | Chong et al. |
| 2011/0066131 A1 | 3/2011 | Cabiri |
| 2011/0092915 A1* | 4/2011 | Olson ............... A61M 5/3202 604/198 |
| 2011/0112504 A1 | 5/2011 | Causey et al. |
| 2011/0125056 A1 | 5/2011 | Merchant |
| 2011/0160654 A1 | 6/2011 | Hanson et al. |
| 2011/0160666 A1 | 6/2011 | Hanson et al. |
| 2011/0160669 A1 | 6/2011 | Gyrn et al. |
| 2011/0172645 A1 | 7/2011 | Moga et al. |
| 2011/0172745 A1 | 7/2011 | Na et al. |
| 2011/0178463 A1 | 7/2011 | Cabiri |
| 2011/0178472 A1 | 7/2011 | Cabiri |
| 2011/0201998 A1 | 8/2011 | Pongpairochana et al. |
| 2011/0224616 A1 | 9/2011 | Slate et al. |
| 2011/0224646 A1 | 9/2011 | Yodfat et al. |
| 2011/0238031 A1 | 9/2011 | Adair et al. |
| 2011/0245773 A1 | 10/2011 | Estes et al. |
| 2011/0270160 A1 | 11/2011 | Mernoe |
| 2011/0282282 A1 | 11/2011 | Lorenzen et al. |
| 2011/0282296 A1 | 11/2011 | Harms et al. |
| 2011/0295205 A1 | 12/2011 | Kaufmann et al. |
| 2011/0313238 A1 | 12/2011 | Reichenbach et al. |
| 2011/0319861 A1 | 12/2011 | Wilk |
| 2011/0319919 A1 | 12/2011 | Curry et al. |
| 2012/0004602 A1 | 1/2012 | Hanson et al. |
| 2012/0010594 A1 | 1/2012 | Holt et al. |
| 2012/0022344 A1 | 1/2012 | Kube |
| 2012/0022496 A1 | 1/2012 | Causey et al. |
| 2012/0022499 A1 | 1/2012 | Anderson et al. |
| 2012/0029431 A1 | 2/2012 | Hwang et al. |
| 2012/0035546 A1 | 2/2012 | Cabiri |
| 2012/0041364 A1 | 2/2012 | Smith |
| 2012/0041387 A1 | 2/2012 | Bruggemann et al. |
| 2012/0041414 A1 | 2/2012 | Estes et al. |
| 2012/0071828 A1 | 3/2012 | Tojo et al. |
| 2012/0096953 A1 | 4/2012 | Bente et al. |
| 2012/0096954 A1 | 4/2012 | Vazquez et al. |
| 2012/0101436 A1 | 4/2012 | Bazargan et al. |
| 2012/0108933 A1 | 5/2012 | Liang et al. |
| 2012/0109059 A1 | 5/2012 | Ranalletta et al. |
| 2012/0118777 A1 | 5/2012 | Kakiuchi et al. |
| 2012/0123387 A1 | 5/2012 | Gonzalez et al. |
| 2012/0129362 A1 | 5/2012 | Hampo et al. |
| 2012/0160033 A1 | 6/2012 | Kow et al. |
| 2012/0165733 A1 | 6/2012 | Bazargan et al. |
| 2012/0165780 A1 | 6/2012 | Bazargan et al. |
| 2012/0172817 A1* | 7/2012 | Bruggemann .... A61M 5/14566 604/218 |
| 2012/0184917 A1 | 7/2012 | Bom et al. |
| 2012/0226234 A1 | 9/2012 | Bazargan et al. |
| 2012/0238961 A1 | 9/2012 | Julian et al. |
| 2012/0259282 A1 | 10/2012 | Alderete et al. |
| 2013/0012875 A1 | 1/2013 | Gross et al. |
| 2013/0068319 A1 | 3/2013 | Plumptre et al. |
| 2013/0085457 A1 | 4/2013 | Schiff et al. |
| 2013/0089992 A1 | 4/2013 | Yang |
| 2013/0096509 A1 | 4/2013 | Avery et al. |
| 2013/0110049 A1 | 5/2013 | Cronenberg et al. |
| 2013/0131589 A1 | 5/2013 | Mudd et al. |
| 2013/0131604 A1 | 5/2013 | Avery |
| 2013/0133438 A1 | 5/2013 | Kow et al. |
| 2013/0172808 A1 | 7/2013 | Gilbert |
| 2013/0190693 A1 | 7/2013 | Ekman et al. |
| 2013/0200549 A1 | 8/2013 | Felts et al. |
| 2013/0204187 A1 | 8/2013 | Avery et al. |
| 2013/0204191 A1 | 8/2013 | Cindrich et al. |
| 2013/0237953 A1 | 9/2013 | Kow et al. |
| 2013/0245595 A1 | 9/2013 | Kow et al. |
| 2013/0245596 A1 | 9/2013 | Cabiri et al. |
| 2013/0245604 A1 | 9/2013 | Kouyoumjian et al. |
| 2013/0253419 A1 | 9/2013 | Favreau |
| 2013/0253420 A1 | 9/2013 | Favreau |
| 2013/0253421 A1 | 9/2013 | Favreau |
| 2013/0253434 A1 | 9/2013 | Cabiri |
| 2013/0267895 A1 | 10/2013 | Hemmingsen |
| 2013/0296799 A1 | 11/2013 | Degtiar et al. |
| 2013/0296824 A1 | 11/2013 | Mo et al. |
| 2013/0304021 A1* | 11/2013 | Cabiri ............... A61M 5/31511 604/506 |
| 2013/0310753 A1 | 11/2013 | Cabiri |
| 2013/0323699 A1 | 12/2013 | Edwards et al. |
| 2013/0331791 A1 | 12/2013 | Gross et al. |
| 2013/0338584 A1 | 12/2013 | Mounce et al. |
| 2014/0018735 A1 | 1/2014 | Causey et al. |
| 2014/0031747 A1 | 1/2014 | Ardehali |
| 2014/0055073 A1 | 2/2014 | Favreau |
| 2014/0055076 A1 | 2/2014 | Favreau |
| 2014/0058349 A1 | 2/2014 | Bazargan et al. |
| 2014/0083517 A1 | 3/2014 | Moia et al. |
| 2014/0094755 A1 | 4/2014 | Bazargan et al. |
| 2014/0121633 A1 | 5/2014 | Causey et al. |
| 2014/0128807 A1 | 5/2014 | Moberg et al. |
| 2014/0128835 A1 | 5/2014 | Moberg et al. |
| 2014/0135692 A1 | 5/2014 | Alderete et al. |
| 2014/0135694 A1 | 5/2014 | Moberg et al. |
| 2014/0142499 A1 | 5/2014 | Moberg et al. |
| 2014/0148784 A1 | 5/2014 | Anderson et al. |
| 2014/0148785 A1 | 5/2014 | Moberg et al. |
| 2014/0163522 A1 | 6/2014 | Alderete et al. |
| 2014/0163526 A1 | 6/2014 | Cabiri et al. |
| 2014/0171881 A1 | 6/2014 | Cabiri |
| 2014/0174223 A1 | 6/2014 | Gross et al. |
| 2014/0194819 A1 | 7/2014 | Maule et al. |
| 2014/0194854 A1 | 7/2014 | Tsals |
| 2014/0207064 A1 | 7/2014 | Yavorsky |
| 2014/0207065 A1 | 7/2014 | Yavorsky |
| 2014/0207066 A1 | 7/2014 | Yavorsky |
| 2014/0213975 A1 | 7/2014 | Clemente et al. |
| 2014/0214001 A1 | 7/2014 | Mortazavi |
| 2014/0228768 A1 | 8/2014 | Eggert et al. |
| 2014/0236087 A1 | 8/2014 | Alderete, Jr. et al. |
| 2014/0243786 A1 | 8/2014 | Gilbert et al. |
| 2014/0261758 A1 | 9/2014 | Wlodarczyk et al. |
| 2014/0343503 A1 | 11/2014 | Holmqvist |
| 2015/0005703 A1 | 1/2015 | Hutchinson et al. |
| 2015/0073344 A1 | 3/2015 | Van Damme et al. |
| 2015/0088071 A1 | 3/2015 | Cabiri |
| 2015/0112278 A1 | 4/2015 | Ray et al. |
| 2015/0119798 A1 | 4/2015 | Gross et al. |
| 2015/0157806 A1 | 6/2015 | Knutsson |
| 2015/0202375 A1 | 7/2015 | Schabbach et al. |
| 2015/0374926 A1 | 12/2015 | Gross et al. |
| 2016/0030665 A1 | 2/2016 | Cabiri |
| 2016/0051756 A1 | 2/2016 | Cabiri |
| 2016/0144117 A1 | 5/2016 | Chun |
| 2016/0151586 A1* | 6/2016 | Kemp ............... A61M 5/2033 604/198 |
| 2016/0175515 A1 | 6/2016 | Mccullough |
| 2016/0184512 A1 | 6/2016 | Marbet et al. |
| 2016/0193406 A1 | 7/2016 | Cabiri |
| 2016/0199590 A1 | 7/2016 | Schabbach et al. |
| 2016/0213840 A1 | 7/2016 | Schabbach et al. |
| 2016/0228652 A1 | 8/2016 | Cabiri et al. |
| 2016/0296713 A1 | 10/2016 | Schader et al. |
| 2016/0296716 A1 | 10/2016 | Cabiri et al. |
| 2016/0331900 A1 | 11/2016 | Wei |
| 2016/0346478 A1 | 12/2016 | Bar-El et al. |
| 2016/0354553 A1 | 12/2016 | Anderson et al. |
| 2017/0007774 A1 | 1/2017 | Brockmeier |
| 2017/0043092 A1 | 2/2017 | Murakami et al. |
| 2017/0058349 A1 | 3/2017 | Levy et al. |
| 2017/0175859 A1 | 6/2017 | Brockmeier |
| 2017/0246399 A1 | 8/2017 | Forlani et al. |
| 2017/0246403 A1 | 8/2017 | Cowe et al. |
| 2018/0028765 A1 | 2/2018 | Waller et al. |
| 2018/0214637 A1 | 8/2018 | Kemp et al. |
| 2019/0022306 A1 | 1/2019 | Gibson et al. |
| 2019/0060578 A1 | 2/2019 | Farris et al. |

(56) References Cited

U.S. PATENT DOCUMENTS

| | | |
|---|---|---|
| 2019/0071217 A1 | 3/2019 | Brown et al. |
| 2019/0175821 A1 | 6/2019 | Kamen et al. |
| 2019/0224415 A1 | 7/2019 | Dugand et al. |
| 2019/0240417 A1 | 8/2019 | Hostettler et al. |
| 2019/0328968 A1 | 10/2019 | Giambattista |
| 2020/0009323 A1 | 1/2020 | Nair et al. |
| 2020/0215270 A1 | 7/2020 | Ogawa et al. |
| 2020/0297929 A1 | 9/2020 | Zhang |
| 2021/0138157 A1 | 5/2021 | Bar-El et al. |
| 2021/0220551 A1 | 7/2021 | Dowd et al. |

FOREIGN PATENT DOCUMENTS

| | | |
|---|---|---|
| CN | 1863566 A | 11/2006 |
| CN | 101090749 A | 12/2007 |
| CN | 101227943 A | 7/2008 |
| CN | 101448536 A | 6/2009 |
| CN | 101522235 A | 9/2009 |
| CN | 101541362 A | 9/2009 |
| CN | 101641126 A | 2/2010 |
| CN | 201692438 U | 1/2011 |
| CN | 201941304 U | 8/2011 |
| CN | 102186733 A | 9/2011 |
| CN | 102378638 A | 3/2012 |
| CN | 105102025 A | 11/2015 |
| DE | 0855313 C | 11/1952 |
| DE | 1064693 B | 9/1959 |
| DE | 19518807 A1 | 12/1995 |
| DE | 19717107 A1 | 11/1998 |
| EP | 0017412 A1 | 10/1980 |
| EP | 0222656 A1 | 5/1987 |
| EP | 0401179 A1 | 12/1990 |
| EP | 0925082 A1 | 6/1999 |
| EP | 1003581 B1 | 11/2000 |
| EP | 1124600 A1 | 8/2001 |
| EP | 1219312 A2 | 7/2002 |
| EP | 1472477 A1 | 11/2004 |
| EP | 1530979 A1 | 5/2005 |
| EP | 1666080 A1 | 6/2006 |
| EP | 1372762 B1 | 2/2007 |
| EP | 1974759 A1 | 10/2008 |
| EP | 2060606 A1 | 5/2009 |
| EP | 2140897 A1 | 1/2010 |
| EP | 2173413 A1 | 4/2010 |
| EP | 2185227 A2 | 5/2010 |
| EP | 2192935 A1 | 6/2010 |
| EP | 2361648 A1 | 8/2011 |
| EP | 2364739 A1 | 9/2011 |
| EP | 2393534 A1 | 12/2011 |
| EP | 2452708 A1 | 5/2012 |
| EP | 2498589 A1 | 9/2012 |
| EP | 2574355 A1 | 4/2013 |
| EP | 2393535 B1 | 3/2015 |
| EP | 2878321 A1 | 6/2015 |
| EP | 2886144 A1 | 6/2015 |
| EP | 1904130 B1 | 3/2016 |
| EP | 2991705 A1 | 3/2016 |
| EP | 3266478 A1 | 1/2018 |
| EP | 2819724 B1 | 3/2019 |
| FR | 2770136 A1 | 4/1999 |
| GB | 2436526 A | 10/2007 |
| JP | 62-112566 A | 5/1987 |
| JP | 01-172843 U | 12/1989 |
| JP | 05-062828 A | 3/1993 |
| JP | 07-194701 A | 8/1995 |
| JP | 3035448 U | 3/1997 |
| JP | H09-505758 A | 6/1997 |
| JP | 11-507260 A | 6/1999 |
| JP | 2000-107289 A | 4/2000 |
| JP | 2000-515394 A | 11/2000 |
| JP | 2001-512992 A | 8/2001 |
| JP | 2002-505601 A | 2/2002 |
| JP | 2002-507459 A | 3/2002 |
| JP | 2002528676 A | 9/2002 |
| JP | 2003-501157 A | 1/2003 |
| JP | 2003-534061 A | 11/2003 |
| JP | 2004-501721 A | 1/2004 |
| JP | 2004-512100 A | 4/2004 |
| JP | 2003-527138 A | 8/2005 |
| JP | 2005-523127 A | 8/2005 |
| JP | 2005-527249 A | 9/2005 |
| JP | 2005-270629 A | 10/2005 |
| JP | 2006-507067 A | 3/2006 |
| JP | 2006-510450 A | 3/2006 |
| JP | 2006-525046 A | 11/2006 |
| JP | 2007-509661 A | 4/2007 |
| JP | 2007-306990 A | 11/2007 |
| JP | 2008-534131 A | 8/2008 |
| JP | 2008-220961 A | 9/2008 |
| JP | 2009502273 A | 1/2009 |
| JP | 2009-101093 A | 5/2009 |
| JP | 2010-540054 A | 12/2010 |
| JP | 2010-540156 A | 12/2010 |
| JP | 2011-136153 A | 7/2011 |
| JP | 2012-100927 A | 5/2012 |
| JP | 4947871 B2 | 6/2012 |
| JP | 2013-500811 A | 1/2013 |
| JP | 2013-505433 A | 2/2013 |
| JP | 2013-517095 A | 5/2013 |
| JP | 2013-519473 A | 5/2013 |
| JP | 2013-530778 A | 8/2013 |
| JP | 2013-531520 A | 8/2013 |
| JP | 2013-531540 A | 8/2013 |
| JP | 2014-030489 A | 2/2014 |
| JP | 2014-515669 A | 7/2014 |
| JP | 2014-518743 A | 8/2014 |
| JP | 2015-514486 A | 5/2015 |
| JP | 2016-525428 A | 8/2016 |
| JP | 2016-530016 A | 9/2016 |
| WO | 90/09202 A1 | 8/1990 |
| WO | 9307922 A1 | 4/1993 |
| WO | 9407553 A1 | 4/1994 |
| WO | 94/15660 A1 | 7/1994 |
| WO | 95/13838 A1 | 5/1995 |
| WO | 96/09083 A1 | 3/1996 |
| WO | 96/32975 A1 | 10/1996 |
| WO | 9700091 A1 | 1/1997 |
| WO | 97/10012 A1 | 3/1997 |
| WO | 97/21457 A1 | 6/1997 |
| WO | 97/33638 A1 | 9/1997 |
| WO | 98/57683 A1 | 12/1998 |
| WO | 98/57686 A1 | 12/1998 |
| WO | 99/29151 A1 | 6/1999 |
| WO | 99/59665 A1 | 11/1999 |
| WO | 00/25844 A1 | 5/2000 |
| WO | 00/69509 A1 | 11/2000 |
| WO | 01/30415 A2 | 5/2001 |
| WO | 200130421 A2 | 5/2001 |
| WO | 01/70304 A1 | 9/2001 |
| WO | 200172357 A2 | 10/2001 |
| WO | 01/89607 A2 | 11/2001 |
| WO | 01/89613 A1 | 11/2001 |
| WO | 0187384 A1 | 11/2001 |
| WO | 02/02165 A2 | 1/2002 |
| WO | 02/04049 A1 | 1/2002 |
| WO | 02/34315 A1 | 5/2002 |
| WO | 200238204 A2 | 5/2002 |
| WO | 02/56934 A2 | 7/2002 |
| WO | 02/56943 A2 | 7/2002 |
| WO | 02072182 A1 | 9/2002 |
| WO | 03/62672 A1 | 7/2003 |
| WO | 03/90833 A1 | 11/2003 |
| WO | 04000397 A1 | 12/2003 |
| WO | 2004/032990 A2 | 4/2004 |
| WO | 2004/098684 A2 | 11/2004 |
| WO | 2004105841 A1 | 12/2004 |
| WO | 2005/018703 A2 | 3/2005 |
| WO | 2005/037350 A2 | 4/2005 |
| WO | 2005/070485 A1 | 8/2005 |
| WO | 2005072795 A2 | 8/2005 |
| WO | 2006018617 A1 | 2/2006 |
| WO | 2006037434 A1 | 4/2006 |
| WO | 2006/052737 A1 | 5/2006 |
| WO | 06069380 A1 | 6/2006 |

(56) References Cited

FOREIGN PATENT DOCUMENTS

| | | |
|---|---|---|
| WO | 2006/102676 A1 | 9/2006 |
| WO | 2006/104806 A2 | 10/2006 |
| WO | 2006121921 A2 | 11/2006 |
| WO | 2007017052 A1 | 2/2007 |
| WO | 2007/056504 A1 | 5/2007 |
| WO | 2007051563 A1 | 5/2007 |
| WO | 2007066152 A2 | 6/2007 |
| WO | 20070073228 A1 | 6/2007 |
| WO | 2007/119178 A2 | 10/2007 |
| WO | 2008/001377 A2 | 1/2008 |
| WO | 2008/014908 A1 | 2/2008 |
| WO | 2008/057976 A2 | 5/2008 |
| WO | 2008/072229 A2 | 6/2008 |
| WO | 2008/076459 A1 | 6/2008 |
| WO | 2008/078318 A2 | 7/2008 |
| WO | 2009/019438 A1 | 2/2009 |
| WO | 2009/022132 A2 | 2/2009 |
| WO | 2009/043000 A1 | 4/2009 |
| WO | 2009/043564 A1 | 4/2009 |
| WO | 2009/046989 A2 | 4/2009 |
| WO | 2009044401 | 4/2009 |
| WO | 2009/069064 A1 | 6/2009 |
| WO | 2009/125398 A2 | 10/2009 |
| WO | 2009144085 A2 | 12/2009 |
| WO | 2010/078227 A1 | 7/2010 |
| WO | 2010/078242 A1 | 7/2010 |
| WO | 2010089313 A1 | 8/2010 |
| WO | 2011/075105 A1 | 6/2011 |
| WO | 2011/090955 A1 | 7/2011 |
| WO | 2011090956 A2 | 7/2011 |
| WO | 2011/101378 A1 | 8/2011 |
| WO | 2011/110872 A1 | 9/2011 |
| WO | 2011/129175 A1 | 10/2011 |
| WO | 2011/133823 A1 | 10/2011 |
| WO | 2011124631 A1 | 10/2011 |
| WO | 2011131778 A1 | 10/2011 |
| WO | 2011131780 A2 | 10/2011 |
| WO | 2011131781 A1 | 10/2011 |
| WO | 2011/156373 A1 | 12/2011 |
| WO | 2012/003221 A1 | 1/2012 |
| WO | 2012/032411 A2 | 3/2012 |
| WO | 2012/040528 A1 | 3/2012 |
| WO | 2012/145752 A2 | 10/2012 |
| WO | 2012/160157 A1 | 11/2012 |
| WO | 2012/168691 A1 | 12/2012 |
| WO | 2013/036602 A1 | 3/2013 |
| WO | 2013/058697 A1 | 4/2013 |
| WO | 2013/115843 A1 | 8/2013 |
| WO | 2014/132293 A1 | 9/2014 |
| WO | 2014/179117 A1 | 11/2014 |
| WO | 2014/179774 A1 | 11/2014 |
| WO | 2014/194183 A2 | 12/2014 |
| WO | 2015/048791 A1 | 4/2015 |
| WO | 2015/048803 A2 | 4/2015 |
| WO | 2015/078868 A1 | 6/2015 |
| WO | 2015/091758 A1 | 6/2015 |
| WO | 2015/091850 A1 | 6/2015 |
| WO | 2015/114428 A1 | 8/2015 |
| WO | 2015/118358 A1 | 8/2015 |
| WO | 2015114158 A1 | 8/2015 |
| WO | 2015163009 A1 | 10/2015 |
| WO | 2016/087626 A1 | 6/2016 |
| WO | 2016/087627 A1 | 6/2016 |
| WO | 2016/141082 A1 | 9/2016 |
| WO | 2018/222521 A1 | 12/2018 |
| WO | 2019/224782 A1 | 11/2019 |
| WO | 2020/120087 A1 | 6/2020 |
| WO | 2020/193468 A1 | 10/2020 |

OTHER PUBLICATIONS

Communication Pursuant to Rules 161 and 162 dated Apr. 6, 2018 in EP Application No. 16784688.0.
Daikyo Crystal Zenith(Registered) polymer, Manufactured by Daikyo Seiko, Lid. (Jun. 25, 2008).
Definition of Monolithic. In Merriam-Webster's online dictionary. Retrieved from https://www.merriam-webster.com/dictionary/monolithic (Year: 2021).
English translation of an Office Action dated Jan. 30, 2013 in CN Application No. 200880117084.X.
English translation of an Office Action dated Mar. 5, 2014 in CN Application No. 200880117084.X.
European Search Report (Partial) dated Mar. 8, 2017 in EP Application 16193157.1.
Extended European Search Report dated Aug. 7, 2014 in EP Application No. 1417477.4.
Extended European Search Report dated Feb. 12, 2018 in EP Application No. 17191756.0.
Extended European Search Report dated Feb. 13, 2017 in EP Application No. 16171626.1.
Extended European Search Report dated Feb. 23, 2015 in EP Application No. 14166591.9.
Extended European Search Report dated Feb. 23, 2015 in EP Application No. 14166596.8.
Extended European Search Report dated Jul. 3, 2017 in EP Application No. 16190054.3.
Extended European Search Report dated Mar. 27, 2014 in EP Application No. 14154717.4.
Extended European Search Report dated Mar. 8, 2016 in EP Application No. 14166592.7.
Extended European Search Report dated Nov. 10, 2016 in EP Application No. 08808111.2.
Extended European Search Report dated Jul. 28, 2020 in European Application No. 20172466.3.
Extended Search Report dated Aug. 7, 2014 in EP Application No. 14171477.4.
Extended Search Report dated Jul. 7, 2017 in EP Application No. 16193157.1.
Int'l Preliminary Report on Patentability dated Nov. 22, 2017 in Int'l Application No. PCT/US2016/068371.
Int'l Search Report and Written Opinion dated Jan. 12, 2011 in Int'l Application No. PCT/US2010/048556; Written Opinion.
Int'l Search Report and Written Opinion dated Jan. 26, 2017 in Int'l Application No. PCT/US2016/056213.
Int'l Search Report and Written Opinion dated Mar. 27, 2017 in Int'l Application No. PCT/US2016/056247.
Int'l Search Report and Written Opinion dated Apr. 21, 2017 in Int'l Application No. PCT/US2016/068367.
Int'l Search Report and Written Opinion dated May 15, 2017 in Int'l Application No. POT/US2016/068371.
Int'l Search Report and Written Opinion dated Jul. 6, 2017 in Int'l Application No. PCT/US2017/022966.
Int'l Search Report and Written Opinion dated Nov. 28, 2016 in Int'l Application No. PCT/US2016/056218.
Int'l Search Report and Written Opinion dated Dec. 2, 2016 in Int'l Application No. PCT/US2016/056210.
Int'l Search Report and Written Opinion dated Dec. 5, 2016 in Int'l Application No. PCT/US2016/056233.
Int'l Search Report and Written Opinion dated Dec. 8, 2016 in Inl'l Application No. PCT/US2016/056227.
Int'l Search Report and Written Opinion dated Dec. 15, 2016 in Inl'l Application No. PCT/US2016/056258.
Int'l Preliminary Report on Patentability dated Jan. 8, 2018 in Int'l Application No. PCTT/US2016/056218.
Int'l Preliminary Report on Patentability dated Apr. 7, 2010 in Int'l Application No. PCT/IL2008/001312.
Int'l Preliminary Report on Patentability dated Aug. 2, 2012 in Int'l Application No. PCT/US2011/021604.
Int'l Preliminary Report on Patentability dated Feb. 7, 2013 in Int'l Application No. PCT/US11/21605.
Int'l Preliminary Report on Patentability dated Jan. 18, 2018 in Int'l Application No. PCT/US2016/056210.
Int'l Preliminary Report on Patentability dated Jan. 18, 2018 in Int'l Application No. PCT/US2016/056213.
Int'l Preliminary Report on Patentability dated Jan. 18, 2018 in Int'l Application No. PCT/US2016/056223.

(56) References Cited

OTHER PUBLICATIONS

Int'l Preliminary Report on Patentability dated Jan. 18, 2018 in Int'l Application No. PCT/US2016/056227.
Int'l Preliminary Report on Patentability dated Jul. 16, 2015 in Int'l Application No. PCT/US2013/078040.
Int'l Preliminary Report on Patentability dated May 14, 2015 in Int'l Application No. PCT/US2013/065211.
Int'l Preliminary Report on Patentability dated Nov. 27, 2014 in Int'l Application No. PCT/US2013/039465.
Int'l Preliminary Report on Patentability dated Nov. 30, 2017 in Int'l Application No. PCT/US2016/068367.
Int'l Preliminary Report on Patentability dated Nov. 9, 2018 in Int'l Application No. PCT/US2016/056238.
Int'l Preliminary Report on Patentability dated Oct. 9, 2014 in Int'l Application No. PCT/US2013/033118.
Int'l Preliminary Report on Patentability dated Sep. 1, 2011 in Int'l Application No. PCT/US2010/048556.
Int'l Search Report and Written Opinion dated Apr. 3, 2014 in Int'l Application No. PCT/US2013/078040.
Int'l Search Report and Written Opinion dated Aug. 5, 2013 in Int'l Application No. PCT/US2013/033118.
Int'l Search Report and Written Opinion dated Jan. 7, 2014 in Int'l Application No. PCT/US2013/065211.
Int'l Search Report and Written Opinion dated Jul. 12, 2017 in Int'l Application No. PCT/US2016/056238.
Int'l Search Report and Written Opinion dated Jul. 26, 2013 in Int'l Application No. PCT/US2012/039465.
Office Action dated Oct. 6, 2020 in Japanese Application No. 2018-538527.
Partial European Search Report dated Nov. 24, 2015 in EP Application No. 14166592.7.
Search Report dated Oct. 14, 2016 in CN Application No. 2014101783742.
U.S. Appl. No. 12/559,563, filed Sep. 15, 2009.
U.S. Appl. No. 12/689,249, filed Jan. 19, 2010.
U.S. Appl. No. 12/689,250, filed Jan. 19, 2010.
U.S. Appl. No. 13/429,840 by Cabiri, filed Mar. 26, 2012.
U.S. Appl. No. 13/472,112 by Cabiri, filed May 15, 2012.
U.S. Appl. No. 13/521,167 by Cabiri, filed Jul. 9, 2012.
U.S. Appl. No. 13/521,181 by Cabiri, filed Jul. 9, 2012.
U.S. Appl. No. 13/643,470 by Alon, filed Oct. 25, 2012.
U.S. Appl. No. 13/733,516 by Cabiri, filed Jan. 3, 2013.
U.S. Appl. No. 13/873,335 by Filman, filed Apr. 30, 2013.
U.S. Appl. No. 13/874,017 by Cabiri, filed Apr. 30, 2013.
U.S. Appl. No. 13/874,085 by Cabiri, filed Apr. 30, 2013.
U.S. Appl. No. 13/874,121 by Degtiar, filed Apr. 30, 2013.
U.S. Appl. No. 13/892,905 by Cabiri, filed May 13, 2013.
U.S. Appl. No. 13/964,651 by Gross, filed Aug. 12, 2013.
U.S. Appl. No. 14/193,692 by Gross, filed Feb. 28, 2014.
U.S. Appl. No. 14/258,661 by Cabiri, filed Apr. 22, 2014.
U.S. Appl. No. 14/553,399 by Cabiri, filed Nov. 25, 2014.
U.S. Appl. No. 14/593,051 by Gross, filed Jan. 9, 2015.
U.S. Appl. No. 14/638,525 by Filman, filed Mar. 4, 2015.
U.S. Appl. No. 14/683,193 by Cabiri, filed Apr. 10, 2015.
U.S. Appl. No. 14/715,791 by Cabiri, filed May 19, 2015.
U.S. Appl. No. 14/725,009 by Bar-El, filed May 29, 2015.
U.S. Appl. No. 14/850,450 by Gross, filed Sep. 10, 2015.
U.S. Appl. No. 14/861,478 by Cabiri, filed Sep. 22, 2015.
U.S. Appl. No. 14/880,673 by Cabiri, filed Oct. 12, 2015.
U.S. Appl. No. 29/479,307 by Norton, filed Jan. 14, 2014.
U.S. Appl. No. 60/997,459, filed Oct. 2, 2007.
West Introduces the Daikyo Crystal Zenith RU Prefillable Syringe, Pharmaceutical Online, Jun. 2008, downloaded from webpage: http://www.pharmaceuticalonline.com/article.mvc/west-introduces-prefillab-le-syringe-system, Download date: Jan. 2009, original posting date: Jun. 2008, 2 pages.
Int'l Search Report and Written Opinion dated Jul. 31, 2014 in Int'l Application No. PCT/US2014/033598.
Int'l Search Report and Written Opinion dated May 13, 2009 in Int'l Application No. PCT/IL2008/001312.
Int'l Search Report dated Apr. 26, 2010 in Int'l Application No. PCT/US2009/069552.
Int'l Search Report dated Jun. 17, 2011 in Int'l Application No. PCT/US2011/021604.
Int'l Search Report dated Oct. 12, 2011 in Int'l Application No. PCT/US11/21605.
Int'l Search Report dated Sep. 22, 2011 in Int'l Application No. PCT/IL11/00368; Written Opinion.
Int'l Written Opinion dated Jul. 19, 2012 in Int'l Application No. PCT/US11/21605.
Intel Search Report and Written Opinion dated Nov. 30, 2016 in Int'l Application No. PCT/US2016/056223.
International Preliminary Report on Patentability and Written Opinion dated Jul. 5, 2011 in International Application No. PCT/US2009/069552.
Notice of Allowance dated Aug. 24, 2015 in U.S. Appl. No. 29/479,307 by Norton.
Offce Action dated Sep. 21, 2010 in U.S. Appl. No. 12/244,666 by Gross.
Office Action dated Apr. 22, 2016 in CN Application No. 2014102892041.
Office Action dated Apr. 5, 2010 in U.S. Appl. No. 12/244,666 by Gross.
Office Action dated Apr. 5, 2010 in U.S. Appl. No. 12/244,688 by Gross.
Office Action dated Aug. 13, 2015 in U.S. Appl. No. 14/553,399 by Cabiri.
Office Action dated Aug. 14, 2017 in CN Application No. 201410178318.9.
Office Action dated Aug. 15, 2013 in CN Application No. 200880117084.X.
Office Action dated Aug. 26, 2014 in CN Application No. 201180006567.4.
Office Action dated Aug. 6, 2014 in EP Appl. No. 11 707 942.6.
Office Action dated Dec. 1, 2015 in CN Application No. 201410289204.1.
Office Action dated Dec. 10, 2013 in CN Application No. 201180006567.4.
Office Action dated Dec. 15, 2017 in U.S. Appl. No. 15/269,248, by Cabiri.
Office Action dated Dec. 17, 2013 in JP Application No. 2012-529808.
Office Action dated Dec. 4, 2017 in CN Application No. 201410178374.2.
Office Action dated Dec. 9, 2016 in U.S. Appl. No. 14/593,051, by Gross.
Office Action dated Feb. 16, 2017 in CN Application No. 2014101783189.
Office Action dated Feb. 20, 2015 in U.S. Appl. No. 13/521,181 by Cabiri.
Office Action dated Feb. 21, 2012 in U.S. Appl. No. 12/689,249.
Office Action dated Feb. 24, 2015 in U.S. Appl. No. 14/258,661 by Cabiri.
Office Action dated Feb. 24, 2017 in U.S. Appl. No. 13/964,651, by Gross.
Office Action dated Feb. 28, 2014 in CN Application No. 201180006571.0.
Office Action dated Feb. 4, 2014 in EP Application No. 11 707 942.6.
Office Action dated Jan. 10, 2017 in U.S. Appl. No. 14/193,692, by Gross.
Office Action dated Jan. 30, 2013 in CN Application No. 200880117084.X.
Office Action dated Jan. 8, 2013 in JP Application No. 2010-527595.
Office Action dated Jan. 8, 2014 in U.S. Appl. No. 13/521,167 by Cabiri.
Office Action dated Jul. 13, 2011 in U.S. Appl. No. 12/559,563 by Cabiri.
Office Action dated Jul. 2, 2012 in U.S. Appl. No. 13/272,555 by Cabiri.
Office Action dated Jul. 28, 2020 in Japanese Application No. 2018-538074.
Office Action dated Jul. 3, 2017 in CN Application No. 2014101783742.

(56) References Cited

OTHER PUBLICATIONS

Office Action dated Jul. 31, 2015 in U.S. Appl. No. 13/521,181 by Cabiri.
Office Action dated Jul. 7, 2014 in U.S. Appl. No. 12/244,666 by Gross.
Office Action dated Jun. 10, 2016 in U.S. Appl. No. 13/964,651 by Gross.
Office Action dated Jun. 14, 2018 in U.S. Appl. No. 13/874,121, by Degtiar.
Office Action dated Jun. 2, 2016 in CN Application No. 2014101783189.
Office Action dated Jun. 3, 2014 in JP Application No. 2010-527595.
Office Action dated Jun. 4, 2015 in U.S. Appl. No. 13/667,739 by Cabiri.
Office Action dated Jun. 9, 2017 in EP Application No. 14166591.9.
Office Action dated Jun. 9, 2017 in EP Application No. 14166596.8.
Office Action dated Mar. 1, 2018 in EP Application No. 14166592.7.
Office Action dated Mar. 10, 2015 in CN Application No. 201180006567.4.
Office Action dated Mar. 10, 2015 in U.S. Appl. No. 12/244,666 by Gross.
Office Action dated Mar. 10, 2015 in U.S. Appl. No. 13/643,470 by Alon.
Office Action dated Mar. 30, 2018 in U.S. Appl. No. 14/850,450 by Gross.
Office Action dated Mar. 31, 2015 in JP Application No. 2012-550068.
Office Action dated Mar. 5, 2014 in CN Application No. 200880117084.X.
Office Action dated May 1, 2015 in U.S. Appl. No. 14/638,525 by Filman.
Office Action dated May 13, 2015 in CN Application No. 201380025566.3.
Office Action dated May 14, 2018 in EP Application No. 08808111.2.
Office Action dated May 16, 2012 in U.S. Appl. No. 12/615,828.
Office Action dated May 18, 2018 in EP 14166591.9.
Office Action dated May 23, 2014 in U.S. Appl. No. 13/472,112 by Cabiri.
Office Action dated May 24, 2017 in U.S. Appl. No. 13/874,121, by Degtiar.
Office Action dated May 25, 2021 in Japanese Office Action 2018-538073.
Office Action dated May 3, 2012 in CN Application No. 200880117084.X.
Office Action dated May 31, 2016 in U.S. Appl. No. 14/593,051 by Gross.
Office Action dated May 4, 2017 in CN Application No. 2014101836665.
Office Action dated May 5, 2015 in CN Application No. 201180006571.0.
Office Action dated May 7, 2015 in JP Application No. 2012-550069.
Office Action dated Nov. 10, 2016 in U.S. Appl. No. 13/874,121, by Degtiar.
Office Action dated Nov. 13, 2017 in U.S. Appl. No. 14/193,692, by Gross.
Office Action dated Nov. 2, 2014 in CN Application No. 201180006571.0.
Office Action dated Nov. 21, 2014 in U.S. Appl. No. 13/429,840 by Cabiri.
Office Action dated Nov. 21, 2014 in U.S. Appl. No. 13/472,112 by Cabiri.
Office Action dated Nov. 25, 2016 in U.S. Appl. No. 13/874,017, by Cabiri.
Office Action dated Nov. 4, 2013 in EP Application No. 11 709 234.6.
Office Action dated Nov. 5, 2013 in JP Application No. 2010-527595.
Office Action dated Nov. 5, 2014 in U.S. Appl. No. 13/643,470 by Alon.
Office Action dated Nov. 8, 2017 in U.S. Appl. No. 13/874,121, by Degtiar.
Office Action dated Oct. 13, 2020 in Japanese Application No. 2018-538073.
Office Action dated Oct. 2, 2018 in JP Application No. 2018-535062 (Year: 2018).
Office Action dated Oct. 28, 2011 in U.S. Appl. No. 12/615,828.
Office Action dated Oct. 28, 2016 in CN Application No. 2014101783742.
Office Action dated Oct. 5, 2016 in U.S. Appl. No. 13/964,651, by Gross.
Office Action dated Oct. 6, 2017 in U.S. Appl. No. 14/861,478, by Cabiri.
Office Action dated Oct. 9, 2014 in U.S. Appl. No. 13/873,335.
Office Action dated Sep. 18, 2015 in U.S. Appl. No. 13/874,085 by Cabiri.
Office Action dated Sep. 2, 2010 in U.S. Appl. No. 12/244,688 by Gross.
Office Action dated Sep. 2, 2014 in JP Application No. 2012-550068.
Office Action dated Sep. 2, 2014 in JP Application No. 2012-550069.
Office Action dated Sep. 28, 2017 in IN Application No. 2528/DELNP/2010.
Office Action dated Sep. 29, 2013 in CN Application No. 201080040968.7.
Office Action dated Sep. 30, 2010 in U.S. Appl. No. 12/689,250, by Cabiri.
Office Action dated Sep. 30, 2015 in U.S. Appl. No. 13/667,739 by Cabiri.
Office Action dated Sep. 6, 2011 in U.S. Appl. No. 12/345,818.
Office Action dated Sep. 9, 2015 in U.S. Appl. No. 13/643,470 by Alon.
Office Action dated Aug. 17, 2021 in Indian Application No. 201827027625.
Office Action dated Nov. 6, 2015 in U.S. Appl. No. 14/715,791 by Cabiri.

* cited by examiner

STAGED TELESCOPIC SCREW ASSEMBLY HAVING DIFFERENT VISUAL INDICATORS

CROSS-REFERENCE TO RELATED APPLICATIONS

This application is a section 371 of International Application No. PCT/US17/22639, filed Mar. 16, 2017, which was published Sep. 21, 2017 under International Publication No. WO 2017/161076 A1, which claims the benefit of U.S. Provisional Application No. 62/309,111, titled "Staged Telescopic Screw Assembly With Color Coding", filed on Mar. 16, 2016, the entire contents of which is incorporated by reference herein.

BACKGROUND OF THE INVENTION

The present invention relates generally to a telescopic screw assembly and more particularly to an injector having a staged telescopic screw assembly with a visual indicator showing the degree of extension of the telescopic screw assembly.

Injectors or syringes are used to deliver specified quantities of drugs or medicine to a patient and typically include a chamber for storing the drug, a needle connected to the chamber through which the drug is delivered, and a plunger which pushes the medicine from the chamber through the needle. One device for pushing the drug through the chamber is a manually activated plunger. The user typically holds the syringe between two fingers and activates or pushes the plunger with a thumb. One drawback of a manually activated plunger is that patients must be relatively dexterous and have the required hand strength to push the plunger themselves. Another apparatus for pushing the plunger through the chamber is a telescopic assembly. A telescopic assembly is generally contained within the syringe and contains a plurality of nested members which expand to push the plunger through the chamber. One drawback of a telescopic assembly is that it can be difficult to tell whether the assembly has properly achieved its maximum extension. Thus, a user may not know whether a full dose of the drug has been administered. Another drawback of the telescopic assembly is that the assembly may extend all at once, or certain of the nested members may extend in a random sequential order.

The present invention addresses the challenges associated with effectively delivering the drug from the chamber through the needle. For example, it is desirable to provide a delivery system that can move the plunger in stages according to a delivery profile based on the drug viscosity, delivery time, and rate of delivery. Furthermore, it is desirable to provide a delivery system that provides a visual indicator to a patient or clinician when a full dose has been administered by an injector.

BRIEF SUMMARY OF THE INVENTION

Briefly stated, one aspect of the present invention is directed to a telescopic screw assembly for an injector comprising an inner screw, an outer screw and a middle screw. The middle screw and the outer screw are in a first threaded engagement, and the inner screw and the middle screw are in a second threaded engagement. The inner screw is nested with the middle screw and the middle screw is nested with the outer screw in a contracted configuration of the screw assembly. Rotation of the outer screw in one rotational direction advances the middle screw relative to the outer screw via the first threaded engagement and advances the inner screw relative to the middle screw via the second threaded engagement to telescopically extend the screw assembly into an expanded configuration. At least two of the inner, middle and outer screws are identified with a different visual indicator to enhance visual distinction between the inner, middle and outer screws, and readily visually indicate an extension progress of the screw assembly. A first rod member is in movable engagement with an inner channel of the inner screw during movement of the screw assembly between the contracted and expanded configurations. A distal end of the first rod member is larger than a proximal end of the inner screw, thereby preventing retraction from the inner screw. A second rod member is in movable engagement with an inner channel of the first rod member during movement of the screw assembly between the contracted and expanded configurations. A distal end of the second rod member is larger than a proximal end of the first rod member, thereby preventing retraction from the first rod member, and a proximal end of the second rod member is fixed to the injector to prevent movement of the second rod member to thereby prevent overextension of the screw assembly.

Briefly stated, another aspect of the present invention is directed to a telescopic screw assembly for an injector comprising an inner screw and an outer screw. The inner screw and the outer screw are in a threaded engagement, and the inner screw is radially nested with the outer screw in a contracted configuration of the screw assembly. Rotation of the outer screw in one rotational direction advances the inner screw relative to the outer screw via the threaded engagement to telescopically extend the screw assembly into an expanded configuration. At least one of the inner and outer screws is identified with a different visual indicator to enhance visual distinction between the inner and outer screws and readily visually indicate an extension progress of the screw assembly. A rod member is in movable engagement with an inner channel of the inner screw during movement of the screw assembly between the contracted and expanded configurations. A distal end of the rod member is larger than a proximal end of the inner channel of the inner screw, and a proximal end of the rod member is fixed to the injector to prevent movement of the rod member to thereby prevent overextension of the screw assembly.

BRIEF DESCRIPTION OF THE DRAWINGS

The following detailed description of a preferred embodiment of the invention, will be better understood when read in conjunction with the appended drawings. For the purpose of illustrating the invention, there is shown in the drawings a preferred embodiment of the telescopic screw assembly which is presently preferred. It should be understood, however, that the invention is not limited to the precise arrangements and instrumentalities shown. In the drawings.

DETAILED DESCRIPTION OF THE INVENTION

Figure 1:
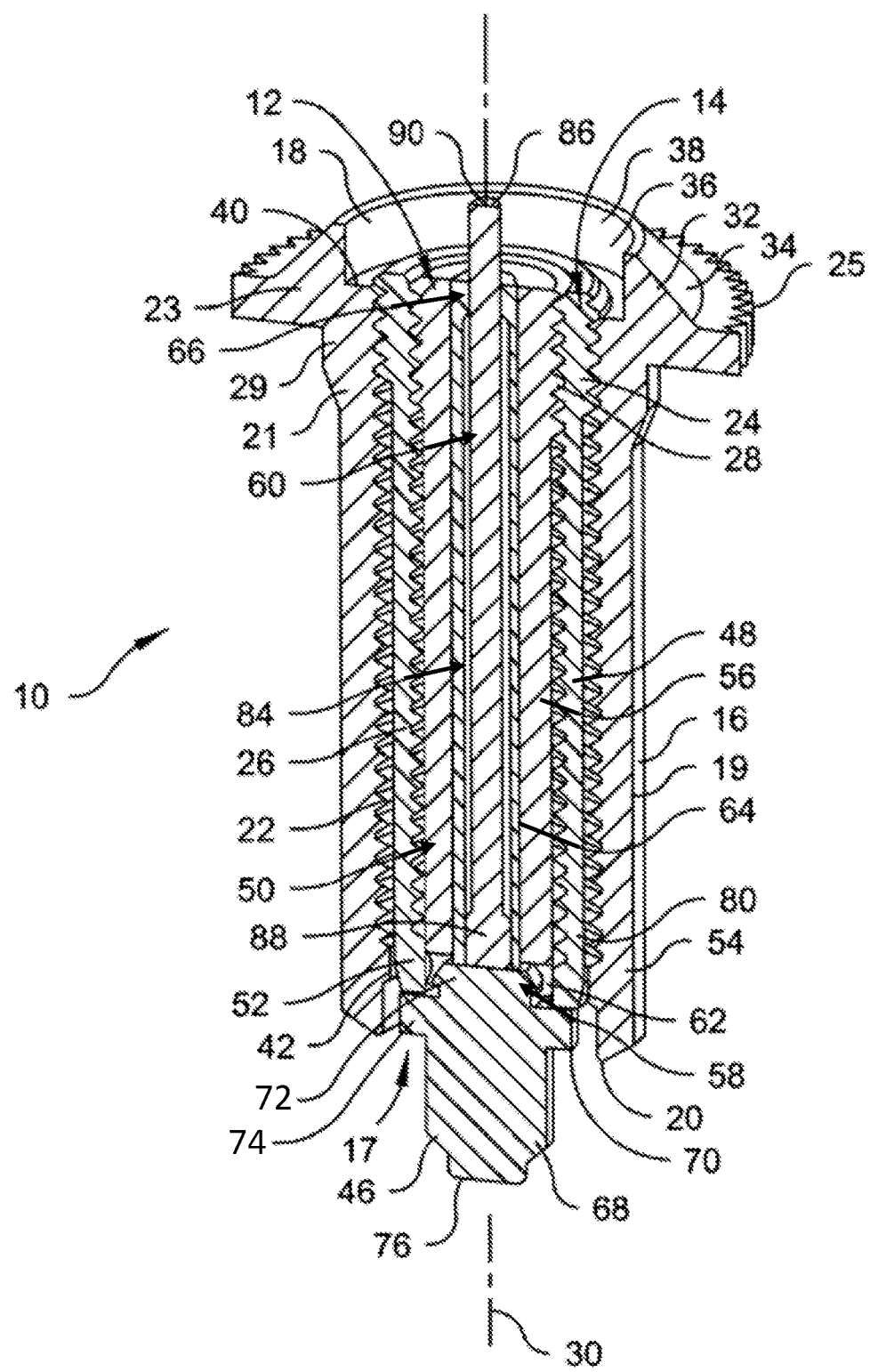
FIG. 1 is a sectional perspective view of a telescopic screw assembly in a contracted configuration in accordance with one embodiment of the present invention.

Certain terminology is used in the following description for convenience only and is not limiting. The words "right," "left," "lower," and "upper" designate directions in the drawings to which reference is made. The words "inwardly" or "distally" and "outwardly" or "proximally" refer to directions toward and away from, respectively, the geometric center or orientation of the telescopic screw assembly and related parts thereof. Unless specifically set forth herein, the terms "a", "an" and "the" are not limited to one element but instead should be read as meaning "at least one". The terminology includes the above-listed words, derivatives thereof and words of similar import.

It should also be understood that the terms "about," "approximately," "substantially" and like terms, used herein when referring to a dimension or characteristic of a component of the invention, indicate that the described dimension/characteristic is not a strict boundary or parameter and does not exclude minor variations therefrom that are functionally similar. At a minimum, such references that include a numerical parameter would include variations that, using mathematical and industrial principles accepted in the art (e.g., rounding, measurement or other systematic errors, manufacturing tolerances, etc.), would not vary the least significant digit.

Figure 2:
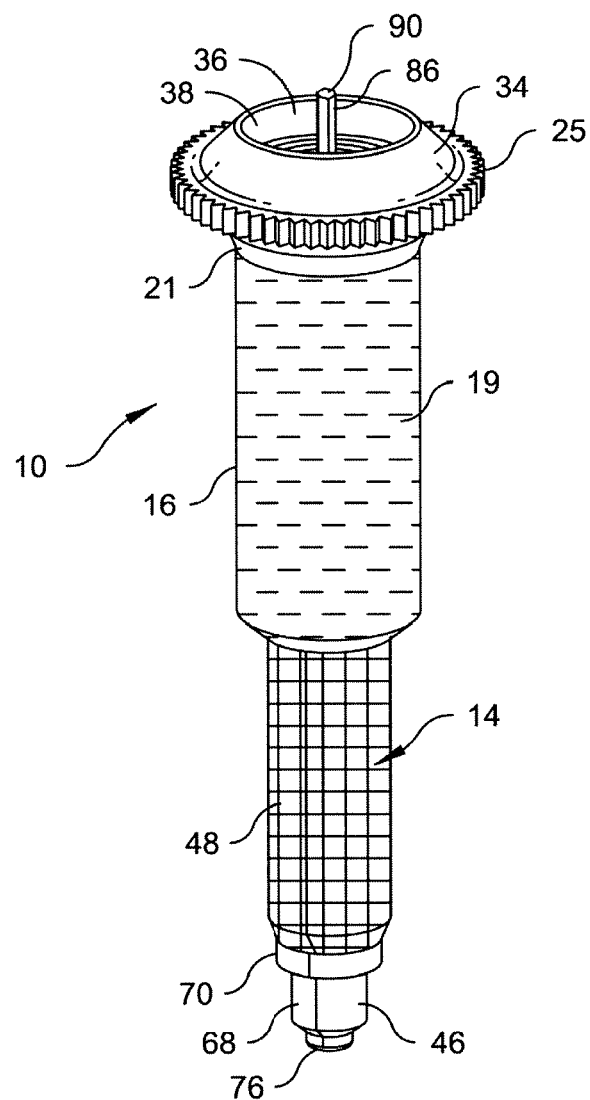
FIG. 2 is a front perspective view of the telescopic screw assembly of FIG. 1 in a partially extended configuration, an outer screw of the telescopic screw assembly being shaded to indicate gray color coding and a middle screw of the telescopic screw assembly being shaded to indicate yellow color coding.
Figure 3:
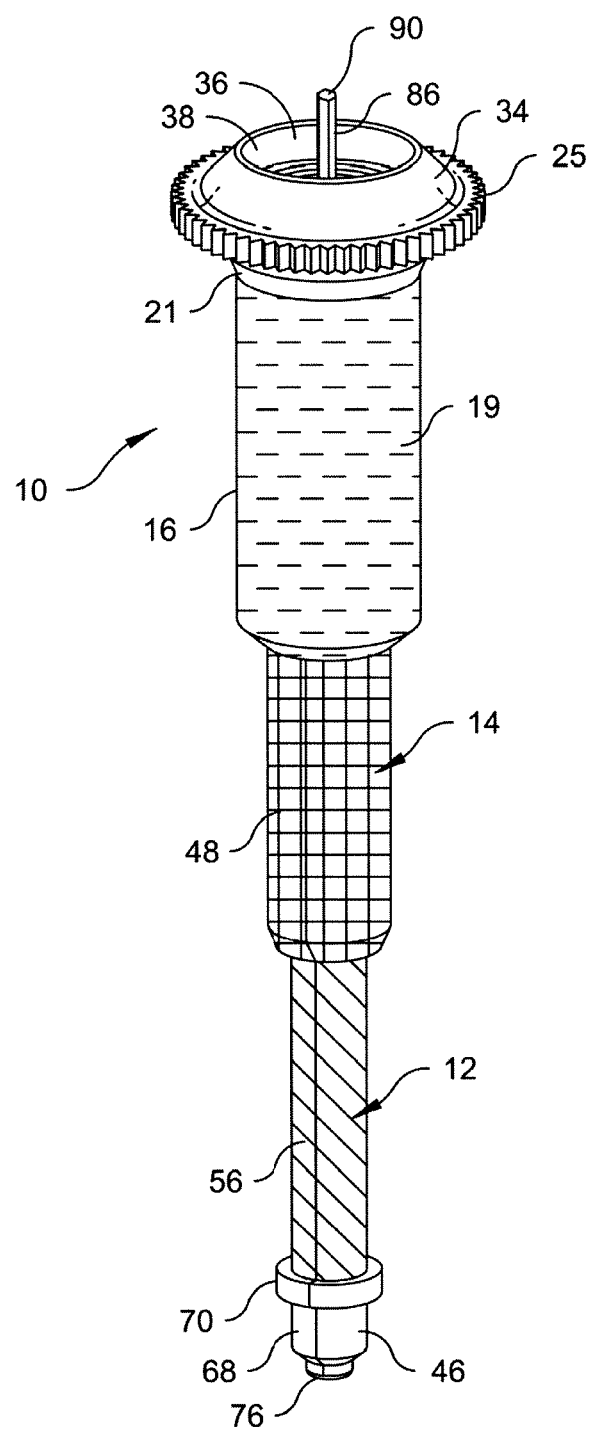
FIG. 3 is a front view of the screw assembly of FIG. 1 in a fully extended configuration, the outer screw being shaded to indicate gray color coding, the middle screw being shaded to indicate yellow color coding, and an inner screw of the telescopic screw assembly being shaded to indicate green color coding.

Referring to FIGS. 1-5, the present application is directed to a telescopic screw assembly in accordance with one embodiment of the present invention, generally designated with reference numeral 10. FIG. 1 is a sectional view of the screw assembly 10 in a contracted configuration which includes an outer screw 16, a middle screw 14, and an inner screw 12 nested inside of one another to allow the screw assembly to telescopically expand to an extended configuration (FIG. 3). The screw assembly 10 can be inserted into an injector 100 or syringe (not shown) to allow the screw assembly 10 to push medicine out of a needle 130 connected to the syringe. One example of an injector contemplated for use with the current invention is disclosed in U.S. Pat. No. 8,157,769, the disclosure of which is hereby incorporated by reference as if fully set forth herein. Each of the outer screw 16, middle screw 14, and inner screw 12 is color coded to allow a user or clinician to observe whether full extension was achieved by the screw assembly 10 to administer a full dose of medicine as explained in greater detail below. Furthermore, the first threaded engagement between the outer screw 16 and middle screw 14, and the second threaded engagement between the middle screw 14 and inner screw 12 have different thread pitches to ensure that the screw assembly 10 extends in a desired sequential order as also explained in greater detail below.

The outer screw 16 includes a body 19 having a generally cylindrical outer shape to fit within an injector 100 having a cylindrical internal cavity (not shown). The outer screw 16 is rotatable with respect to the injector 100. A neck 21 extends upwardly from the body 19 and serves as a transition between the body 19, which has a smaller diameter than the neck 21, and a head 23, which has a larger diameter than the neck 21. The neck 21 has a shape to minimize any stress concentrations that may be present in the outer screw 16. An upper wall 29 extends upwardly from the neck 21 and abuts the head 23. The upper wall 29 has a generally cylindrical shape with a diameter sized to maintain the position of the screw assembly 10 within the injector 100.

The head 23 includes a gear 25 which is oriented to rotate about an axis 30 extending between a proximal end 18 and a distal end 20 of the screw assembly 10. The gear 25 is adapted to engage an element of the injector 100 or syringe (element not shown, but could be a thumb wheel, a gear attached to a motor or similar driving mechanism, etc.) to rotate the gear 25, and thus, the outer screw 16. As should be understood by one of ordinary skill in the art, any suitable type of gear could be adopted (e.g. spur gear, helical gear, bevel gear). The proximal end 18 of the head 23 has a proximal portion 32 which extends upwardly and radially inwardly from the gear 25. The outer surface 34 of the proximal portion 32 has a frustoconical shape, while the inner surface 36 of the proximal portion 32 is an annular wall 38 extending upwardly from a shoulder 40 and defines a recess within the proximal portion 32 above the shoulder 40.

Although the outer screw 16 is shown with the body 19, neck 21, and head 23 all formed as a monolithic element, the body 19, neck 21, or head 23 could each be formed as a separate element and connected to the other elements of the outer screw 16 by traditional fastening methods (e.g. welding, adhesive, screws, or the like). Furthermore, the outer screw 16 (as well as any other elements of the screw assembly 10) can be manufactured from plastic, polymers, stainless steel, etc. by traditional methods (e.g. molding, additive manufacturing, machining, or the like). An opening 17 extends through the outer screw 16 from the proximal end 18 to the distal end 20. As should be understood by one of ordinary skill in the art, the opening 17 need not extend completely through the proximal end 18 of the outer screw 16. However, an opening 17 which does extend through the proximal end 18 facilitates easier loading of the middle screw 14 into the opening 17. The opening 17 is sized to receive an inner screw 12 and a middle screw 14. Alternatively, the screw assembly 10 can omit a middle screw 14 or include more than one middle screw 14. An outer screw inner thread 22 is formed along at least a portion of the opening 17, and preferably, along a majority of the opening 17. The outer screw inner thread 22 can have any desired thread pitch provided that it mates with a middle screw outer thread 24. A protrusion 42 is formed at the distal end 20 of the inner thread 22 and extends generally perpendicularly away and radially inwardly from the outer screw 16 and into the opening 17 to prevent movement of the middle screw 14 distally beyond the protrusion 42.

The middle screw 14 has a generally cylindrical, tubular shape designed to fit within the opening 17 with a length equal to or at least slightly less than that of the outer screw 16 such that the middle screw 14 fits completely within the opening 17 when the screw assembly 10 is in the contracted configuration best seen in FIG. 1. The middle screw 14 includes an unthreaded portion 48 which has an outer diameter less than the diameter of the outer screw inner thread 22 and less than the inner diameter of the protrusion 42 to allow the unthreaded portion 48 to move within the opening 17 and beyond the protrusion 42. A middle screw outer thread 24 is formed on the proximal end 18 of the middle screw 14 which includes threads having a pitch which meshes with the outer screw inner thread 22 such that rotation of the outer screw 16 relative to the middle screw 14 advances the middle screw 14 (distally or downwardly when viewing FIGS. 1-4) along the axis 30. Of course, the middle screw outer thread 24 could be formed anywhere along the middle screw 12 if desired. However, the distance the outer thread 24 extends toward the distal end 20 of the middle screw 14 limits the travel distance of the middle screw 14 because of the interference between the protrusion 42 and the outer thread 24 as the middle screw 14 moves distally within the opening 17.

Figure 4:
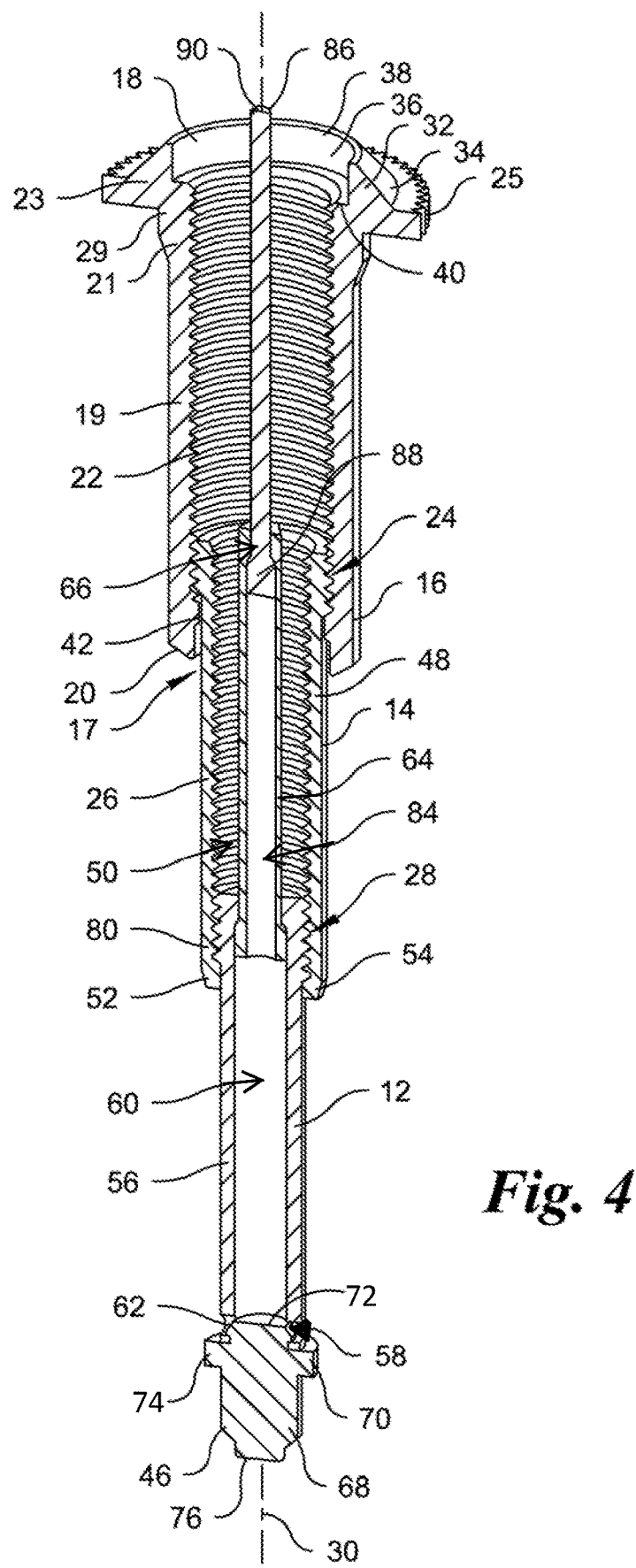
FIG. 4 is a sectional view of the screw assembly of FIG. 1 in a fully extended configuration.
Figure 5:
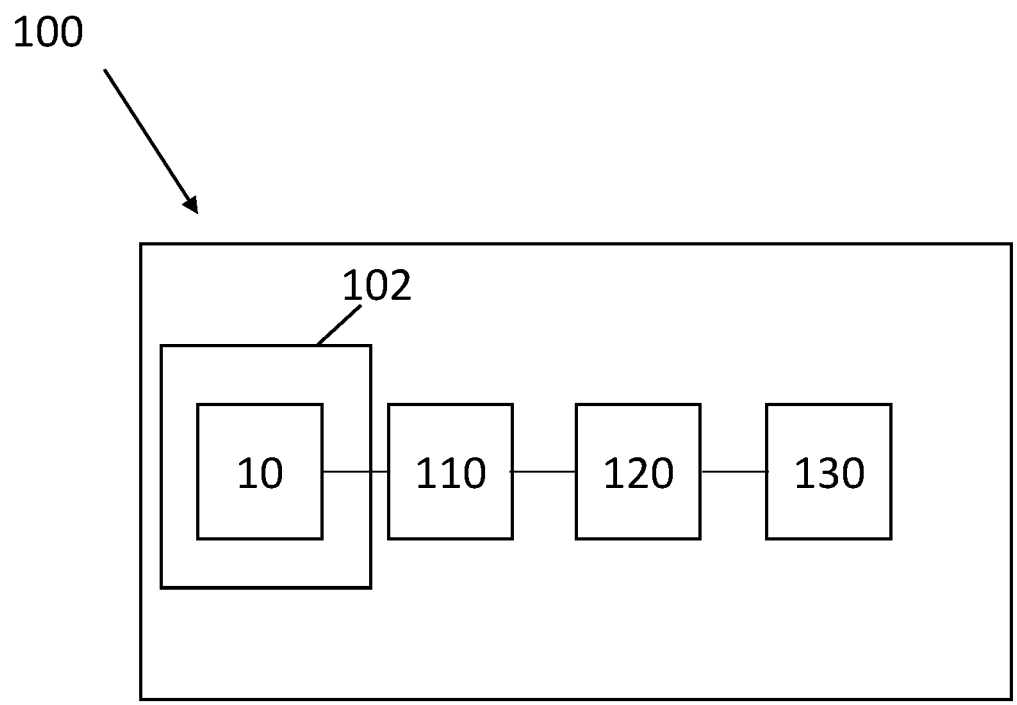
FIG. 5 is a schematic illustration of an injector employing the telescopic screw assembly of FIG. 1.

A cylindrical passageway 50 extends through the middle screw 14 from the proximal end 18 to the distal end 20 with a middle screw inner thread 26 formed thereon. The pitch of the middle screw outer thread 24 is preferably different from, but can be the same as, the pitch of the middle screw inner thread 26. More preferably, the pitch of the outer thread 24 is smaller than the pitch of the inner thread 26. The passageway 50 includes a radially inwardly extending projection 52 at the distal end of the passageway 50 as shown in FIGS. 1 and 4 to prevent movement of the inner screw 12 when the inner screw outer thread 28 contacts the projection 52. Alternatively, the projection 52 can be positioned anywhere along the passageway 50. The distal end of the middle screw 14 has a chamfer 54 which facilitates insertion of the middle screw 14 into the opening 17 of the outer screw 16 from the proximal end 18. The middle screw 14 has an outer diameter sized to prevent a cap 46 on the distal end of the inner screw 12 from entering the passageway 50.

The inner screw 12 has a generally cylindrical, tubular shape and is positionable within the passageway 50. The inner screw 12 includes an unthreaded portion 56 which has a smaller diameter than the inner screw outer thread 28 and is sized to rotate within the passageway 50 to move along the axis 30 and through the opening defined by the projection 52. An inner screw outer thread 28 is formed adjacent the proximal end of the inner screw 12 and engages the middle screw inner thread 26. The threaded engagement between the inner screw outer thread 28 and middle screw inner thread 26 causes movement of the inner screw 12 along the axis 30 as the middle screw 14 is rotated relative to the inner screw 12.

As should be understood by one of ordinary skill in the art, the difference in thread pitches of the middle screw outer thread 24 and the middle screw inner thread 26 ensures that as a rotational force is applied to the gear 25, the middle screw 14 advances distally along the axis 30 before the inner screw 12 moves, as best seen in FIG. 2. As the rotational force continues to be applied to the gear 25, the inner screw 12 only begins to move once the middle screw outer thread 22 contacts the protrusion 42 and the middle screw 14 can no longer advance. After this contact, the middle screw 14 begins to rotate as the rotational force continues to be applied to the gear 25 and causes the inner screw 12 to extend distally, as best seen in FIGS. 3-4. Of course, the pitch of the middle screw outer thread 24 can be relatively large, provided that the pitch of the middle screw inner thread 26 is larger. As should be understood by one of ordinary skill in the art, the size of the pitch on either thread 24, 26 can influence the delivery profile and can be based on drug viscosity, delivery time, rate of delivery of the drug, and other factors. Alternatively, the pitch of the threads 24, 26 could be changed to ensure that the inner screw 12 moves first, that the inner screw 12 and middle screw 14 extend simultaneously, that both extend simultaneously but one extends faster than the other, etc. One advantage of controlling the stages of delivery is it ensures that the screw assembly 10 provides its strongest extension force for the greatest amount of time.

A generally cylindrical channel 60 extends through the inner screw 12 and is sized to receive a first member 64. The channel 60 has a generally smooth surface to allow the first member 64 to slide along the length of the channel 60. The proximal portion 66 of the channel 60 defines a narrower opening than the rest of the channel 60 to prevent the first member 64 from exiting the channel 60. A pocket 62 is formed in the distal portion 58 of the channel 60 to secure the cap 46 to the inner screw 12. The pocket 62 can be a continuous pocket which extends completely around the internal surface of the channel 60, or can be one or more individual pockets which extend only partially around the channel 60 to receive individually formed protrusions on the cap 46. Alternatively, the inner screw 12 could be formed without the pocket 62 and a press-fit, screw, weld, etc. could be used to couple the cap 46 to the inner screw 12. In yet another alternative, the cap 46 and inner screw 12 could be formed as a monolithic element, thus avoiding the need for any coupling element between the two.

The cap 46 has a cylindrical base 68 with a collar 70 extending radially away from the base 68. The collar 70 is generally cylindrical and has a larger outer diameter than the diameter of the middle screw passageway 50 to prevent the collar 70 from entering the passageway 50 by contacting the distal end of the middle screw 14. Of course, the base 68 could have a wide enough diameter that the collar 70 can be omitted. A stem 72 extends upwardly from the base 68 and is sized to extend into the channel 60. The length of the stem 72, as measured along the axis 30, is such that a flange 74 aligns with the pocket 62. The flange 74 extends outwardly from the stem 72 and is configured to be positioned in the pocket 62 to secure the cap 46 to the inner screw 12. A threaded tail 76 extends downwardly from the base 68 and is configured to engage a plunger 110 which can push medicine through a chamber 120 of the injector 100 as the telescopic screw assembly 10 moves form the contracted configuration (FIG. 1) through the partially extended configuration (FIG. 2) to the fully extended configuration (FIGS. 3-4).

The first member 64 has a generally cylindrical, tubular structure with a length preferably shorter than the inner screw 12 such that the first member 64 remains within the channel 60 when the screw assembly 10 is in the contracted configuration shown in FIG. 1. The first member 64 has an outer diameter sized to allow movement within the channel 60, and can include an outwardly extending flare (not shown) on the distal end 80 which contacts a reduced diameter segment (not shown) on the proximal end of the inner screw 12 to prevent the first member 64 from exiting the channel 60 as the screw assembly 10 moves between the contracted configuration shown in FIG. 1 to the extended configuration shown in FIGS. 3-4. The first member 64 includes a generally cylindrical passageway 84 sized to receive a second member 86. The passageway 84 includes the narrow proximal portion 66 which slides along the second member 86 but is prevented from going past a flared portion 88 of the second member 86 as best seen in FIG. 4.

The second member 86 is a generally cylindrical rod positioned within the passageway 84. The proximal end 90 of the second member 86 can be fixed by a snap fit, set screw, etc. to the injector 100 to prevent movement of the second member 86. One advantage of fixing the second member 86 to the injector 100 is to prevent overextension of the screw assembly 10 via the various interference fits between the elements of the assembly 10.

The outer screw 16, middle screw 14, and inner screw 12 can each include a visual indicator to allow a clinician to observe the progress of the administering of the drug and whether the screw assembly 10 achieved full extension when administering a dose via the injector 100. In one embodiment, for example, without limitation, the outer screw 16 is gray, the middle screw 14 is yellow, and the inner screw 12 is green, and all are readily observable through a transparent, translucent, or open window 102 of the injector 100. As should be understood by one of ordinary skill in the art, the colors selected for the screws 12, 14, 16 can be any desired color scheme suitable to permit visual distinction between the outer, middle, and inner screws 16, 14, 12. Alternatively, stripes, dots, hatching, etc. could be used to distinguish the screws 12, 14, 16 from one another instead of a solid color. One advantage of such an indicator is that a patient can observe whether the injection is complete or if continued application of the injector to the injection site is required. Furthermore, such an indicator allows a clinician or failure investigation team to determine is a drug was used as prescribed or intended.

In use, a user places a cartridge or chamber 120 containing the drug in the injector 100 and may input information regarding the drug into the injector 100 to allow the injector 100 to determine maximum flow rate, viscosity, etc. from which the injector 100 can calculate the optimal expansion rate and torque to apply to the screw assembly 10. The user then activates the screw assembly 10 by pressing a button, activating a thumb wheel, voice command etc. (not shown). The outer screw 16 begins to turn when a rotational force is applied to the gear 25. As the outer screw 16 rotates, the middle screw 14 is moved from the contracted configuration (FIG. 1) to the partially expanded configuration (FIG. 2). Once the middle screw outer thread 24 contacts the protrusion 42 the middle screw 14 can no longer move distally. The middle screw 14 then begins to rotate as the rotational force continues to be applied to the gear 25. As the middle screw 14 rotates, the inner screw 12 moves from the contracted configuration within the middle screw 14 (FIG. 2) to the fully expanded configuration (FIGS. 3-4). A plunger 110 connected to the cap 46 pushes through the chamber 120 to transfer the drug out of the chamber 120 via the needle 130 connected to the chamber 120 as the middle screw 14 and inner screw 12 move distally. The user receives visual indication regarding the degree of expansion of the screw assembly 10 from the visual indicators (e.g. colors) of the inner, middle, and outer screws 12, 14, 16. Once the drug delivery is complete, an opposite rotational force can be applied to the gear 25 to return the screw assembly 10 to the contracted configuration.

It will be appreciated by those skilled in the art that changes could be made to the embodiments described above without departing from the broad inventive concept thereof. It is understood, therefore, that this invention is not limited to the particular embodiment(s) disclosed, but it is intended to cover modifications within the spirit and scope of the present invention, as set forth in the appended claims.

We claim:
1. An injector, comprising:
an injector window;
a chamber within the injector and configured to store a substance therein;
a plunger within the injector;
a needle within the injector and connected to the chamber; and
a telescopic screw assembly within the injector and externally observable through the injector window, the telescopic screw assembly configured to engage the plunger to push the substance out of the chamber and through the needle, the telescopic screw assembly comprising:
an inner screw, an outer screw and a middle screw,
the middle screw and the outer screw being in a first threaded engagement, and the inner screw and the middle screw being in a second threaded engagement, the inner screw being nested with the middle screw and the middle screw being nested with the outer screw in a contracted configuration of the telescopic screw assembly,
wherein rotation of the outer screw in one rotational direction advances the middle screw relative to the outer screw via the first threaded engagement and advances the inner screw relative to the middle screw via the second threaded engagement to telescopically extend the telescopic screw assembly into an expanded configuration, and
the inner, middle and outer screws being identified with different visual indicators from one another to enhance visual distinction between the inner, middle and outer screws and readily visually indicate an extension progress of the telescopic screw assembly to indicate whether a full dose of the substance has been administered;
a first rod member having a cylindrical body in movable engagement with an inner channel of the inner screw during movement of the telescopic screw assembly between the contracted and expanded configurations, a distal end of the first rod member being larger than a proximal end of the inner screw, thereby preventing retraction from the inner screw; and
a second rod member having a cylindrical body in movable engagement with an inner channel of the first rod member during movement of the telescopic screw assembly between the contracted and expanded configurations, a distal end of the second rod member being larger than a proximal end of the first rod member, thereby preventing retraction from the first rod member, and a proximal end of the second rod member being fixed to the injector to prevent movement of the second rod member to thereby prevent overextension of the telescopic screw assembly.

2. The injector of claim 1, wherein the different visual indicators of the inner, middle and outer screws is a different color coding of the inner, middle and outer screws.

3. The injector of claim 1, wherein the outer screw comprises a body and a gear proximate a proximal end of the body, the gear being configured to engage a driving member to rotate the outer screw about a central axis thereof.

4. The injector of claim 1, wherein the outer screw includes an inner channel extending therethrough, the inner channel of the outer screw being sized to receive the middle screw and the inner screw.

5. The injector of claim 4, wherein the inner channel of the outer screw includes an inner thread along at least a portion thereof, and a radially inwardly extending protrusion proximate a distal end of the inner thread, the protrusion being sized to prevent distal advancement of a proximal end of the middle screw beyond the protrusion.

6. The injector of claim 5, wherein the middle screw includes an unthreaded outer portion having an outer diameter less than a diameter of the inner thread of the outer screw and less than an inner diameter of the protrusion, whereby the unthreaded outer portion of the middle screw is distally advanceable through the inner channel of the outer screw and beyond the protrusion thereof.

7. The injector of claim 6, wherein the middle screw further includes an outer thread proximate a proximal end thereof, the outer thread of the middle screw defining a complementary pitch with a pitch of the inner thread of the outer screw and meshing therewith to define the first threaded engagement.

8. The injector of claim 7, wherein the middle screw further comprises an inner passageway extending therethrough, the inner passageway of the middle screw being sized to receive the inner screw.

9. The injector of claim 8, wherein the middle screw further comprises an inner thread along at least a portion of the inner passageway thereof, the inner thread of the middle screw defining a different pitch from the pitch of the outer thread of the middle screw.

10. The injector of claim 9, wherein the pitch of the outer thread of the middle screw is smaller than the pitch of the inner thread of the middle screw.

11. The injector of claim 8, wherein the inner passageway of the middle screw includes a radially inwardly extending projection at a distal end thereof, the radially inwardly extending projection being sized to prevent distal advancement of a proximal end of the inner screw beyond the radially inwardly extending projection.

12. The injector of claim 11, wherein the inner screw comprises an outer thread proximate a proximal end thereof, the outer thread of the inner screw defining a complementary pitch with the pitch of the inner thread of the middle screw and meshing therewith to define the second threaded engagement.

13. The injector of claim 12, wherein the inner screw further comprises an unthreaded outer portion having an outer diameter less than a diameter of the inner thread of the middle screw and less than an inner diameter of the radially inwardly extending projection, whereby the unthreaded outer portion of the inner screw is distally advanceable through the inner passageway of the middle screw and beyond the radially inwardly extending projection thereof.

14. The injector of claim 8, further comprising a cap secured to a distal end of the inner screw, the cap being engageable with the plunger, and wherein the inner passageway of the middle screw is sized to prevent the cap from entering the inner passageway.

15. The injector of claim 1, wherein the inner channel of the inner screw defines a generally smooth inner surface and the proximal end of the inner screw defines a narrower opening than a diameter of the inner channel of the inner screw.

16. The injector of claim 15, wherein the distal end of the first rod member is radially outwardly flared relative to a remainder of the first rod member.

17. The injector of claim 1, wherein the first rod member defines a length equal to, or less than, a length of the inner screw.

18. The injector of claim 1, wherein the inner channel of the first rod member defines a generally smooth inner surface and the proximal end of the first rod member defines a narrower opening than a diameter the inner channel of the first rod member.

19. The injector of claim 18, wherein the distal end of the second rod member is radially outwardly flared relative to a remainder of the second rod member.

20. An injector comprising:
an injector window;
a chamber within the injector and configured to store a substance therein;
a plunger within the injector;
a needle within the injector and connected to the chamber; and
a telescopic screw assembly within the injector and externally observable through the injector window, the telescopic screw assembly configured to engage the plunger to push the substance out of the chamber and through the needle, the telescopic screw assembly comprising:
an inner screw and an outer screw,
the inner screw and the outer screw being in a threaded engagement, and the inner screw being radially nested with the outer screw in a contracted configuration of the telescopic screw assembly, wherein rotation of the outer screw in one rotational direction advances the inner screw relative to the outer screw via the threaded engagement to telescopically extend the telescopic screw assembly into an expanded configuration, and
the inner and outer screws being identified with different visual indicators from one another to enhance visual distinction between the inner and outer screws and readily visually indicate an extension progress of the telescopic screw assembly to indicate whether a full dose of the substance has been administered; and
a rod member having a cylindrical body in movable engagement with an inner channel of the inner screw during movement of the telescopic screw assembly between the contracted and expanded configurations, a distal end of the rod member being larger than a proximal end of the inner channel of the inner screw, and a proximal end of the rod member being fixed to the injector to prevent movement of the rod member to thereby prevent overextension of the telescopic screw assembly.

21. The injector of claim 20, wherein the different visual indicators of the inner and outer screws is a different color coding of the inner and outer screws.

22. The injector of claim 20, wherein the outer screw comprises a body and a gear proximate a proximal end of the body, the gear being configured to engage a driving member to rotate the outer screw about a central axis thereof.

* * * * *